(12) United States Patent
Shibusawa et al.

(10) Patent No.: US 7,342,130 B2
(45) Date of Patent: Mar. 11, 2008

(54) METHOD FOR PRODUCING ACRYLIC ACID

(75) Inventors: Fumio Shibusawa, Himeji (JP);
Masaru Ishikawa, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/634,133

(22) Filed: Dec. 6, 2006

(65) Prior Publication Data

US 2007/0129572 A1    Jun. 7, 2007

(30) Foreign Application Priority Data

Dec. 6, 2005 (JP) ............................ 2005-352719
Jul. 10, 2006 (JP) ............................ 2006-189542

(51) Int. Cl.
*C07C 51/42* (2006.01)
*C07C 51/16* (2006.01)

(52) U.S. Cl. ...................................... 562/523; 562/600
(58) Field of Classification Search ................ 562/523, 562/598, 532
See application file for complete search history.

(56) References Cited

U.S. PATENT DOCUMENTS

| | | |
|---|---|---|
| 3,868,410 A | 2/1975 | Horlenko et al. |
| 5,897,749 A | 4/1999 | Kroker et al. |
| 6,383,973 B1 | 5/2002 | Kimura et al. |
| 6,482,981 B2 | 11/2002 | Ueno et al. |
| 6,498,272 B1 | 12/2002 | Schröder et al. |
| 6,870,066 B2 | 3/2005 | Shibusawa et al. |
| 2004/0015014 A1 | 1/2004 | Nishimura et al. |
| 2004/0220426 A1* | 11/2004 | Yada et al. .................. 562/513 |
| 2004/0220427 A1 | 11/2004 | Yada et al. |

FOREIGN PATENT DOCUMENTS

| | | |
|---|---|---|
| EP | 0 887 334 | 12/1998 |
| EP | 1 162 192 | 12/2001 |

(Continued)

*Primary Examiner*—Karl Puttlitz
(74) *Attorney, Agent, or Firm*—Wenderoth, Lind & Ponack, L.L.P.

(57) ABSTRACT

A method for producing acrylic acid, comprising (a) a absorption step of absorbing acrylic acid-containing gas obtained by oxidizing raw material gas in gas phase as crude acrylic acid-containing solution, (b1) a step of separating high boiling point components that separates the crude high boiling point components at a distillation column as (b) a step of purifying the acrylic acid-containing solution, and further, (c) a decomposition step of decomposing Michael adducts contained in the high boiling point components to prepare acrylic acid and (d) a collection step of collecting acrylic acid generated in the decomposition step (c), whereby the proportion of the amount of maleic acid to a sum of the sum of the maleic acid and maleic anhydride in the high boiling point components that are fed from the high boiling point component separation step (b1) to the decomposition step (c) satisfies a equation below:

[Equation 1]

$$\frac{[\text{Maleic acid (mass)}]}{[\text{Maleic acid (mass)}] + [\text{Maleic anhydride(mass)}]} \times 100 \leq 70\%. \quad (1)$$

12 Claims, 5 Drawing Sheets

FOREIGN PATENT DOCUMENTS

| | | |
|---|---|---|
| JP | 47-40621 | 10/1972 |
| JP | 49-55614 | 5/1974 |
| JP | 53-41637 | 11/1978 |
| JP | 8-206504 | 8/1996 |
| JP | 9-110778 | 4/1997 |
| JP | 11-12222 | 1/1999 |
| JP | 2000-325795 | 11/2000 |
| JP | 2001-199931 | 7/2001 |
| JP | 1 162 192 | 12/2001 |
| JP | 2001-348358 | 12/2001 |
| JP | 2001-348359 | 12/2001 |
| JP | 2001-348360 | 12/2001 |
| JP | 2002-539104 | 11/2002 |
| JP | 2003-160532 | 6/2003 |
| JP | 2003-171342 | 6/2003 |
| JP | 2003-246765 | 9/2003 |
| JP | 2003-321418 | 11/2003 |
| JP | 2004-51489 | 2/2004 |
| JP | 2005-15478 | 1/2005 |

\* cited by examiner

METHOD FOR PRODUCING ACRYLIC ACID

BACKGROUND OF THE INVENTION

1. Field of the Invention

The present invention relates to a method for producing acrylic acid and more specifically, relates to a method for producing acrylic acid from acrylic acid solution at high yield.

2. Description of the Related Art

In a process for producing acrylic acid by carrying out the catalytic gas phase oxidation of propylene and/or acrolein, it has been known that Michael adducts such as the dimer to pentamer and oligomer of acrylic acid are generated as by-products by the action of heat and its catalyst at purification step, in addition to water, acids such as propionic acid, acetic acid and maleic acid, acetone, aldehydes such as acrolein, furfural and formaldehyde at catalytic gas phase oxidation reaction. These by-products become cause for preventing the stable operation of the production of acrylic acid and reducing the yield of acrylic acid as a desired product. Further, since acrylic acid is a easily polymerizing substance, there have been problems that the polymer of acrylic acid is prepared at a synthesis step of accompanying heating and a purification step such as distillation to cause blocking in an apparatus and product yield is reduced. Various technologies are proposed for solving the problems and stably and efficiently producing acrylic acid.

In the patent literatures 1 to 4 described later, there are described processes for producing acrylic acid that adopted a distillation purification process by which gaseous acrylic acid obtained by the catalytic gas phase oxidation is caught as an acrylic acid solution and by-products contained in the solution are removed by distillation. In these technologies, a process of suppressing the polymerization of acrylic acid and a process of decomposing the Michael adducts and collecting them as acrylic acid are also proposed.

For example, in U.S. Patent Application Publication No.2004015014 (JP-A-2004-51489, hereinafter, called as "Patent Literature 1"), it is described that a polymerization inhibitor is fed from the specific position of an absorption column and a distillation colon so that the polymerization inhibitor is uniformly dispersed and there is described a process of providing coolers between respective steps, suppressing the generation of polymers by cooling feed solution and further, decomposing acrylic acid oligomer (Michael adducts) using a thin-film evaporator and a thermal decomposing vessel to collect acrylic acid. In the specification of European Patent Application Publication No.0887334 (JP-A-11-12222, hereinafter, called as "Patent literature 2") and JP-A-2003-160532 (hereinafter, called as "Patent Literature 3"), there is proposed a process of decomposing the Michael adducts using a reaction-distillation apparatus, a distillation column equipped with a thin-film evaporator and a thermal decomposing vessel and collecting acrylic acid. Further, in JP-A-2003-246765 (hereinafter, called as "Patent Literature 4"), there is described a process of decomposing acryl multimer (Michael adducts) contained in the bottom solution (effluent) of an acrylic acid purification column to acrylic acid and collecting it to improve the yield of acrylic acid.

SUMMARY OF THE INVENTION

Further, in the above-mentioned patent literatures, it is also indicated that maleic acid prepared as a by-product in the production step of acrylic acid reduces the yield of acrylic acid and prevents the stable operation of production. Maleic acid is prepared as a by-product at synthesis of acrylic acid and exists in a state of water-including maleic acid (under environment in which water exists at low temperature) or in a state of maleic anhydride (under environment in which water does not exist at high temperature) depending on a composition in the process. In particular, since the solubility of maleic acid in acrylic acid is low, it is easily precipitated and a copolymer with acrylic acid is also easily formed.

However, it is difficult to completely remove water prepared in a synthesis step and water used in an absorbing step from the system in the above-mentioned production step of acrylic acid; therefore maleic acid is hardly dehydrated under environment in which water exists thus and becomes an easily precipitated state. Further, when maleic acid is heated, it is easily transferred to fumaric acid, but since these maleic acid and fumaric acid are easily precipitated in comparison with maleic anhydride, they raise the viscosity of an acrylic acid solution to reduce the decomposition efficiency of the Michael adducts and cause the blockage of pipes in production apparatuses and staining.

Concerning a problem with respect to such maleic acid, it is described in the patent literature 1 that a maleic acid separation column is used to reduce the quantity of maleic acid in decomposition solution after thermal decomposition (the decomposition of the Michael adducts). In the patent literatures 2 and 3, it is described that the quantity of maleic acid simultaneously collected with acrylic acid is reduced by controlling reaction temperature and operation pressure at the decomposition reaction of the Michael adducts and thus, the accumulation of maleic acid or maleic anhydride in the collection system is prevented.

However, there is a limit for reducing the quantity of maleic acid and maleic anhydride only by optimizing the conditions of decomposition and collection and there is fear that the accumulation quantity of maleic acid in the system is increased during continuous operation.

Further, in the patent literature 4, there is described a method of positively adding water and non water-soluble solvent in advance of the decomposition of the Michael adducts or to collection solution after the decomposition of the Michael adducts and precipitating maleic acid to be separated. However, the establishment of new step requires further facility investment and causes result raising the production cost of acrylic acid. Further, the increase of the quantity of solvent used is also not preferable from the viewpoints of economy and environment.

The present invention has been carried out focusing attention on the above-mentioned circumstances. It is the purpose of the present invention to provide a method, in particular, by suppressing problems derived from maleic acid (or example, such as the blockage of piping and apparatuses and pressure increase in apparatuses) and trouble such as the deterioration of property of solution containing a high boiling point component, efficiently promoting the decomposition of the Michael adducts and producing acrylic acid at high yield when acrylic acid is collected from high boiling point components containing the Michael adducts that are separated from acrylic acid at purification step.

As a result of intensively studying solution focusing attention on the above-mentioned problems, the present inventors have found that in the production process of acrylic acid in particular, when the Michael adducts contained in high boiling point components separated from acrylic acid is decomposed to be collected as acrylic acid, troubles such as the precipitation of maleic acid at a decomposition step thereafter, stain caused by the occurrence of copolymers with acrylic acid, the rising of viscosity and pressure loss in a column are suppressed by reducing the quantity of water-including maleic acid contained in the high boiling point components to a specific quantity or less. Namely, it is difficult to reduce the total amount of maleic acid formed as a by-product at the reaction step, but it has been cleared that if the amount of (water-including) maleic acid that is included by the presence of water at the purification step is reduced and further this is dehydrated (maleic anhydride), troubles derived from maleic acid in the decomposition step is suppressed and acrylic acid is efficiently collected.

The process for producing acrylic acid of the present invention solved the above-mentioned problems has a purpose that it comprises (a) an absorption step of absorbing acrylic acid-containing gas obtained by oxidizing raw material gas in gas phase as crude acrylic acid-containing solution, (b1) a high boiling point component separation step that separates the high boiling point components at a distillation column as (b) a step of purifying the acrylic acid-containing solution, and further, (c) a decomposition step of decomposing Michael adducts contained in the high boiling point components to give acrylic acid and (d) a collection step of collecting acrylic acid generated in the decomposition step (c), wherein the proportion of an amount of maleic acid to the sum of the maleic acid and maleic anhydride in the high boiling point components that are fed from the high boiling point component separation step (b1) to the decomposition step (c) is 70% or less (which is a value calculated from the following equation (1) and also the proportion of the amount of maleic acid when the sum of maleic acid and maleic anhydride is referred to as 100%).

[Equation 1]

$$\frac{[\text{Maleic acid (mass)}]}{[\text{Maleic acid (mass)}] + [\text{Maleic anhydride (mass)}]} \times 100 \leq 70\% \quad (1)$$

As described above, since the solubility of maleic acid to acrylic acid is low and easily precipitated in comparison with maleic anhydride, the copolymer of maleic acid with acrylic acid and maleic acid are hardly precipitated in the decomposition step when the amount of maleic acid fed to the decomposition step is preliminarily reduced. Further, since low boiling components such as water are already removed from the high boiling point components usually fed to the decomposition step, water is eliminated from maleic acid during decomposition treatment and dehydrated. Since the melting point of maleic anhydride formed at that time is low, it can exist in the high boiling point components in a melt state.

Consequently, the stable decomposition of the Michael adducts and the efficient collection of acrylic acid can be carried out without occurring the blockage of piping and pressure increase in apparatuses according to the above-mentioned process of the present invention, namely, by setting the amount of water-including maleic acid contained in the high boiling point components and the amount of water-including maleic acid for the total amount of water-including maleic acid and maleic anhydride as a specified amount or less.

Further, in the present specification, the "low boiling point substance" means a substance in which boiling point is lower than acrylic acid at a standard condition (25° C. and atmospheric pressure) and the "high boiling point substance" means a substance in which boiling point is higher than acrylic acid at a standard condition.

Further, the "Michael adducts" means the multimer of acrylic acid shown in the undermentioned general formula (1). The example of the Michael adducts includes β-acryloxypropionic acid and a salt thereof in case of an acrylic acid dimer.

[Chem.1]

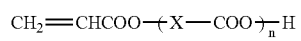
(1)

(Provided that in the formula (1), n represents an integer of 1 to 5 and —X— represents —$CH_2CH_2$— or —CH($CH_3$)—. Further, when n is 2 or more, a plural number of —X—'s may be the same or different.)

Further, the "purification" includes distillation, diffusion, crystallization, extraction, absorption and the like. Hereat, the "distillation" is a process of heating solution to its boiling point and separating a volatile component included and the "crystallization" means that a desired product is separated as crystal.

Further, in the present specification, "maleic acid" means "water-including maleic acid" unless otherwise specifically noticed and used separately from maleic anhydride.

DESCRIPTION OF THE PREFERRED EMBODIMENT

Figure 1:
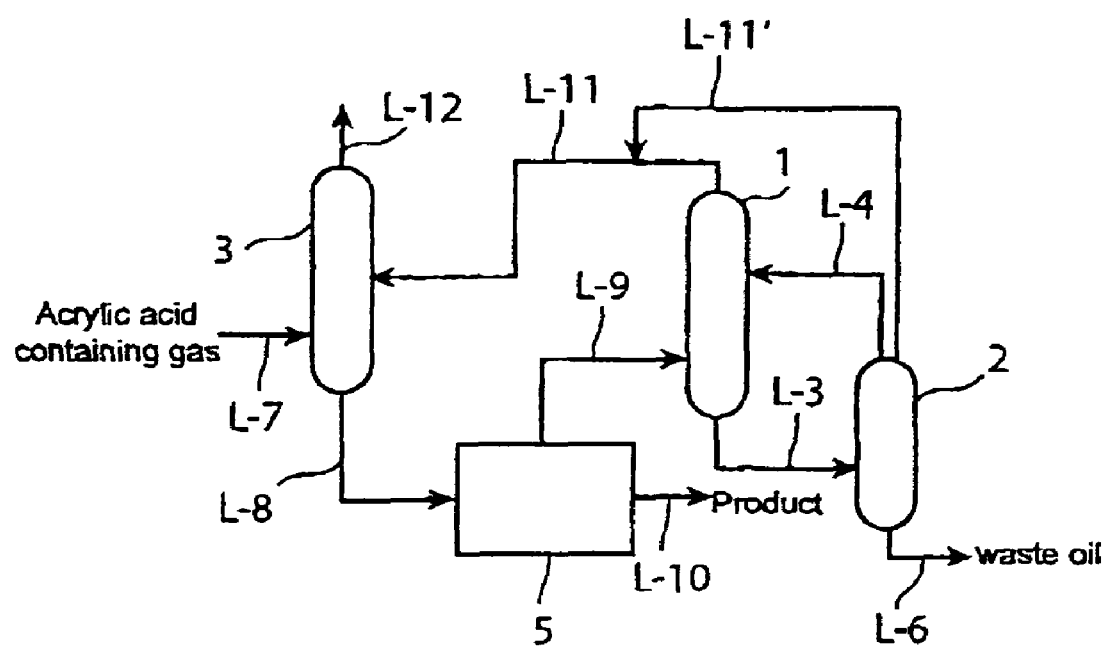
FIG. 1 is a step diagram showing one example of the step of the process for producing acrylic acid related to the present invention.

The process for producing acrylic acid of the present invention has characteristic in that it comprises (a) an absorption step of absorbing acrylic acid-containing gas obtained by oxidizing raw material gas in gas phase as crude acrylic acid-containing solution, (b1) a high boiling point component separation step that separates the high boiling point components at a distillation column as (b) a step of purifying the crude acrylic acid-containing solution and further, (c) a decomposition step of decomposing Michael adducts contained in the high boiling point components to generate acrylic acid and (d) a collection step of collecting the acrylic acid generated in the decomposition step (c), wherein the proportion of an amount of maleic acid to a sum of maleic acid and maleic anhydride in the high boiling point components fed from the high boiling point component separation step (b1) to the decomposition step (c) is 70% or less (which is a value calculated from the following equation (1) and also the proportion of the amount of maleic acid when the sum of maleic acid and maleic anhydride is referred to as 100%).

[Equation 1]

$$\frac{[\text{Maleic acid (mass)}]}{[\text{Maleic acid (mass)}] + [\text{Maleic anhydride (mass)}]} \times 100 \leq 70\% \quad (1)$$

As described above, when the proportion (the proportion of an amount of water-including maleic acid for the total amount of maleic acid (water-including maleic acid+maleic anhydride)) of the amount of maleic acid in the high boiling point components fed to the decomposition step is set as the above-mentioned range, precipitate at the decomposition step and the generation of pressure increase in an apparatus can be suppressed; therefore the decomposition of the Michael adducts can be efficiently carried out and acrylic acid can be stably produced.

The proportion of the amount of maleic acid in the high boiling point components calculated from the above-mentioned equation (1) is preferably 50% or less and more preferably 40% or less. Needless to say, it is needless to say that the proportion of the amount of maleic acid is most preferably 0%.

However, in order to make the proportion of the amount of maleic acid to 0%, severe operation condition is occasionally adapted to a specific step (the stable operation property of production step is occasionally damaged) and the production efficiency of acrylic acid must be occasionally sacrificed. Accordingly, it is difficult in real operation that the proportion of the amount of maleic acid calculated from the above-mentioned equation (1) is set as 0%, and it is not preferable from the viewpoint of economy. Further, the lower limit of the proportion of the amount of maleic acid calculated by the above-mentioned equation (1) is usually a value larger than 0%. Specifically, the lower limit of the proportion of the amount of maleic acid is preferably 5%, more preferably 10%, and most preferably 20%.

The above-mentioned high boiling point components is a component containing a component with higher boiling point than acrylic acid and contains by-products at the production of acrylic acid including the Michael adducts. Further, it is the purpose of the present invention to further improve the production efficiency of acrylic acid by collecting acrylic acid from the high boiling point components. Furthermore, as described above, the present invention has characteristic in that the quantity of maleic acid in the high boiling point components fed to the decomposition step is reduced to a specific amount or less. Consequently, in the present invention, the synthesis process of acrylic acid is not limited at all and either of the production processes of acrylic acid conventionally known can be employed. For example, as a solution containing the above-mentioned high boiling point components, those discharged from the purification step (for example, the above-mentioned distillation, dispersion, crystallization, extraction, absorption and the like), or those separated from acrylic acid being a product in a further purification step that is arbitrarily provided, if necessary, after passing the purification step. Needless to say, acrylic acid may be contained in the solution containing the high boiling point components. Typical example includes the bottom solution of the distillation column, residual mother liquid generated by crystallization purification and the like.

Further, as the industrial production process of acrylic acid, a process of catalytically oxidizing propylene and/or acrolein in gas phase is general. Therefore, in the present specification, a case that catalytic gas phase oxidation process is employed as the synthesis process of acrylic acid is illustrated as an example.

Respective steps are specifically illustrated below referring to drawings accordingly.

[Synthesis of Acrylic Acid]

Acrylic acid raw materials such as propylene and/or acrolein are mixed with molecular oxygen-containing gas such as air and diluted gas to prepare raw material gas. The raw material gas is fed to a reactor filled with a catalytic gas phase oxidation catalyst and acrylic acid-containing gas is obtained by the catalytic gas phase oxidation reaction.

Condition at the catalytic gas phase oxidation reaction is not specifically limited and processes conventionally known may be employed. Further, recycle gas (described later) generated at the acrylic acid collecting step described later may be used for the above-mentioned raw material gas. The reactor carrying out the catalytic gas phase oxidation reaction is not specifically limited, but a multi tubular reactor is preferably used because reaction efficiency is superior.

The catalytic gas phase oxidation catalyst conventionally known is filled in the above-mentioned reactor and oxidation is carried out by bringing the raw material gas in contact with molecular oxygen-containing gas such as oxygen and air. When propylene is used as the raw material gas, it is preferable that the concentration of propylene is 7 to 15% by volume, water is 0 to 10% by volume and molecular oxygen is a range of propylene: molecular oxygen (volume ratio) =1:1.0 to 2.0. As the feed source of the above-mentioned molecular oxygen, air may be used. Further, when air contains moisture, it is preferable to preliminarily remove moisture before feeding air to the reactor. The reason is that the reduction of moisture content introduced into the reactor is the reduction of moisture content introduced into the acrylic acid absorption step (a). Further, oxygen-enriched air, pure oxygen and the like may be used in place of air. As dilution gas, nitrogen, carbon dioxide, other inactive gas and the like can be used.

In the present invention, after recycle gas discharged from the absorption column 3 (refer to FIG. 1) described later is cooled and condensable substances are condensed, it may be introduced into the reactor (not illustrated). The reason is that an unreacted raw material and the like are occasionally contained in the recycle gas. When the recycle gas is used, it is preferable to preliminarily remove moisture in the recycle gas so that moisture concentration in the raw material gas fed to the reactor is preferably 0 to 10% by volume, more preferably 0 to 7% by volume and further preferably 0 to 6% by volume. When moisture content is too much, the loss rate of acrylic acid may be increased by moisture fed to the absorption column through the reactor. Further, it is preferable that total acid concentration in the recycle gas is preferably 0 to 0.2% by volume and more preferably 0 to 0.1% by volume. When the total acid concentration is within the above-mentioned range, the deterioration of the catalyst is hardly generated and the catalytic gas phase oxidation reaction proceeds stably. Unreacted propylene, acrolein, oxygen, dilution gas and the like are also contained in the recycle gas in addition to moisture and an acid component.

The above-mentioned propylene, oxygen, moisture concentration and the total acid concentration can be easily adjusted when moisture content contained in the recycle gas, the blending amount of raw material gas, propylene concentration and oxygen concentration contained in the recycle gas are calculated so that moisture concentration and the total acid concentration in the raw material gas are to be within the above-mentioned range and propylene concentration and air concentration that are newly fed to the reactor are determined. Further, the "total acid" represents compounds having a carboxyl group and acrylic acid, formic acid, acetic acid and the like are contained in the recycle gas.

The catalytic gas phase oxidation reaction in case of using propylene as a raw material is usually carried out at two stages and two kinds of the catalytic gas phase oxidation catalysts are used. The catalyst at the first stage is a catalyst that oxidizes the raw material gas containing propylene in gas phase and mainly generates acrolein, and the catalyst at the second stage oxidizes the raw material gas containing acrolein in gas phase and mainly generates acrylic acid. As the catalyst at the first stage, complex oxide containing iron, molybdenum and bismuth can be mentioned and as the catalyst at the second stage, a catalyst in which vanadium is an essential component can be mentioned.

Further, the catalytic gas phase oxidation reaction may be a mode of carrying out the above-mentioned two stage reaction in a single reactor and may be a mode of carrying out it in tandem connecting two different reactors.

The acrylic acid-containing gas obtained by the catalytic gas phase oxidation reaction contains unreacted components in the raw material gas and reaction by-products such as propionic acid, maleic acid, acetone, acrolein, furfural, formaldehyde and $CO_x$ (carbon monoxide, carbon dioxide and the like) together with 5 to 14% by volume of acrylic acid, 0.1 to 2.5% by volume of acetic acid, 0.5 to 3% by volume of molecular oxygen and 5 to 36% by volume of water.

[Acrylic Acid Absorption Step (a)]

Then, the acrylic acid-containing gas obtained is brought in contact with an absorption solvent and fed to the absorption column 3 absorbing as an acrylic acid-containing solution (the absorption step (a)). Hereat, a distillate from the reaction-distillation apparatus 2 (reaction apparatus) that carries out the decomposition of the Michael adducts (the decomposition step (c)) may be introduced to the absorption column 3 in addition to the above-mentioned acrylic acid-containing gas. The distillate includes acrylic acid as the decomposition product of the Michael adducts in high concentration and acrylic acid is obtained at high yield by collecting the distillate. Further, details are described later, but the distillate from the reaction-distillation apparatus 2 is preferably those passing through the high boiling point component separation step (b1) that separates the high boiling point components (distillation column 1).

The above-mentioned absorption column is not specifically limited so far as it can adequately bring acrylic acid gas in contact with an absorption solvent absorbing acrylic acid and for example, known absorption columns such as a plate column, a packed column, a wetted-wall column and a spray column may be used.

The above-mentioned acrylic acid-containing gas is fed from the bottom side of the absorption column and on the other hand, a absorption solvent is fed from the top side of the absorption column. At this time, the contact process of the acrylic acid-containing gas with the absorption solvent is not limited and for example, there can be employed either of known contact processes such as cross flow contact using a bubble tray, a uniflat tray, a porous plate tray, a jet tray, a bubble tray and a venturi tray; counter flow contact using regular filler and irregular filler of turbo grid tray, a dual flow tray, a ripple tray, a Kittel tray, gauge type, sheet type and grid type.

The above-mentioned absorption solvent is not specifically limited so far as it can absorb and dissolve acrylic acid, but those conventionally known such as, for example, high boiling point organic solvents such as diphenyl ether, diphenyl, o-dimethyl phthalate and a mixture of diphenyl ether with diphenyl; water; water containing organic acid generated from the acrylic acid purification process and acrylic acid solution and ejector waste water can be widely used. Further, in the present specification, the above-mentioned "high boiling point organic solvent" includes an organic solvent having higher boiling point than acrylic acid, or a mix solvent containing the organic solvent. The above-mentioned acrylic acid purification process includes the above-mentioned steps (a) to (d) after the catalytic gas phase oxidation step. Accordingly, the water containing organic acid generated from the acrylic acid purification process and acrylic acid solution include, for example, the bottom solution of the absorption column and the like, reflux liquid, condensate cooling gas components discharged from the top side of the absorption column and the like for the absorption column for the absorption process (a); residues separated from acrylic add which is a product by various purification processes and the like for the purification step (b); bottom solution of the column, solution extracted from the middle of a column, reflux liquid, distillate and the like for the decomposition step (c) and the high boiling point component separating step (b1).

The amount of an absorption solvent fed to the absorption column may be suitably determined depending on the desired concentration of the acrylic acid-containing solution. Further, the acrylic acid concentration of the acrylic acid-containing solution is good as high as possible from the viewpoint of efficiently carrying out the purification step (b). From the viewpoint, the ratio of mass flow rate of the absorption solvent introduced into the absorption column is 0.1 to 1.5-times of the mass flow rate of the acrylic acid contained in acrylic acid-containing solution, preferably 0.1 to 1.0-times and more preferably 0.15 to 0.8-times and it is preferable that acrylic acid is collected by bringing acrylic acid in counter flow contact with the acrylic acid-containing gas. The lowering of the absorbing efficiency of the acrylic acid absorption column is suppressed by setting the ratio of mass flow rate within the above-mentioned range and the acrylic acid-containing solution with high concentration is obtained.

In order to prevent the polymerization of polymerizing substances such as acrylic acid in the absorption column, a polymerization inhibitor may be added to the above-mentioned absorption solvent. The polymerization inhibitor includes one or more of compounds selected from the group consisting of an N-oxyl compound, a phenol compound, a manganese salt such as manganese acetate, a copper salt of dialkyldithiocarbamate such as copper dibutylthiocarbamate, a nitroso compound, an amine compound and phenothiazine that are described in JP-A-2001-348360, JP-A-2001-348358, JP-A-2001-348359 and the like.

It is recommended to operate the acrylic acid absorption column at a column top pressure (gauge pressure) of 0 to 0.4 MPa, preferably 0 to 0.1 MPa and further preferably 0 to 0.03 MPa When the column top pressure is too low, a reduced pressure apparatus is required and facility cost and utilities cost become high. On the other hand, the column top pressure is too high, the temperature of the absorption column is required to be raised for discharging the low boiling substance from the top side of the absorption column; therefore the absorption efficiency of acrylic acid may be lowered. Acrylic acid may be efficiently absorbed by setting the column top pressure as the above-mentioned range. Further, the temperature of the top side of the absorption column is preferably 30 to 85° C. and more preferably 40 to 80° C.

Further, in the process of the present invention, condensate obtained by cooling the portion (recycle gas) of discharge gas discharged from the top side of the absorption column may be used as the portion of the absorption solvent. Since the condensate contains often acrylic acid, the absorption yield of acrylic acid may be heightened by utilizing it as the absorption solvent. Further, when the condensate is utilized, it is preferable to introduce the condensate to absorption column by adjusting it at 0 to 50° C. Ten to 40° C. is more preferable. The recycle gas after separation of the condensate may be also used as the portion of the raw material gas at synthesis of acrylic acid.

Further, in the present specification, among gas discharged from the top side of the absorption column, the discharge gas circulated to the reactor (synthesis of acrylic acid) is referred to as the "recycle gas" and gas discharged from the top side of the absorption column to outside of the system is referred to as "waste gas".

The cooling process of the recycle gas is not limited and an apparatus that can condense a condensable substance contained in the recycle gas may be used. For example, a multi tubular heat exchanger, a fin tube type heat exchanger, an air-cooled heat exchanger, a double-pipe heat exchanger, a coil type heat exchanger, a direct contact type heat exchanger, a plate type heat exchanger and the like can be used.

Further, the amount of the condensate introduced into the absorption column is preferably 20 to 70% in the absorption solvent. 30 to 55% is more preferable.

The crude acrylic acid-containing solution obtained by the present step is fed from the bottom side of the absorption column 3 through the line L-8 to the purification apparatus 5 that carries out the separation and purification of acrylic acid (the purification step (b)). Further, acrylic acid as a product, acrolein as the raw material and the like in addition to the by-product at the catalytic gas phase oxidation reaction may be contained in the bottom solution of the absorption column 3. Consequently, an acrolein separation step for removing acrolein may be provided before feeding to the purification apparatus 5, if necessary.

[Purification Step (b)]

Then, the acrylic acid-containing solution obtained in the absorption column 3 is extracted from the bottom side of the absorption column 3 and fed to the purification apparatus 5 (purification step) through the line L-8 (FIG. 1). The purification process is not specifically limited and purification processes conventionally known such as, for example, a distillation purification process, a crystallization purification process, a film separation process and a chemical treatment process may be used alone or a combination thereof may be used.

For example, when the distillation purification process is employed, there may be employed an azeotropic separation process by which distillation is carried out in the presence of an azeotropic solvent and pure acrylic acid-containing solution is obtained from crude acrylic acid-containing solution.

As the distillation column that may be used for the azeotropic separation process, known columns such as a plate column, a packed column, a wetted-wall column and a spray column can be used. The azeotropic solvent includes toluene, heptane, dimethylcyclotoluene, methyl isobutyl ketone, ethyl acrylate, methyl methacrylate, hexane, butyl acetate and the like.

Further, the treatment temperature of the crystallization purification process among the above-mentioned purification processes is low in comparison with the distillation purification process and the generation of the polymer of acrylic acid and the Michael adducts is also little. Accordingly, it is one of the preferable modes in the present invention to employ the crystallization purification process as the purification step. Then, a case of employing the crystallization purification process is illustrated below (the crystallization purification step (b2) of acrylic acid).

[Crystallization Purification Step (b2) of Acrylic Acid]

When the crystallization purification process is employed as the purification step (b), the crude acrylic acid-containing solution obtained in the absorption step (a) is fed to the crystallization apparatus (the purification apparatus 5) and acrylic acid is separated as crystal to be purified (the crystallization purification step (b2)). In the process for producing acrylic acid related to the present invention, the crystal of acrylic acid obtained in the crystallization purification step (b2) is provided for purification step of carrying out rinsing, sweating and the like if necessary, and it is more preferable that acrylic acid having higher panty is produced.

The crystallization process adoptable in the crystallization purification step (b2) is not limited, either of a continuous process or a batch-wise process may be employed and it may be carried out at one stage or 2 stages or more.

As the continuous crystallization apparatus; a tower type BMC (Backmixing Column Crystallizer) type crystallizer (manufactured by Nippon Steel Chemical Co., Ltd.) in which a crystallization part, a solid-liqud separation part and a crystal purification part are integrated; a crystallization apparatus in which a crystallization part (for example, CDC (Cooling Disk Crystallizer) crystallizer manufactured by GMF GOUDA Co.), a solid liquid separation part (for example, belt filter, centrifugal machine and the like) and a crystal purification part (for example, KCP (Kureha Crystal Purifier) manufactured by Kureha Techno Engineering Co., Ltd. and the like) are combined; may be used.

Hereat, there is specifically illustrated a case that a continuous crystallization apparatus that combines a crystallizer in which two crystallizers (CDC) described in "KAGAKU SOUCHI (Chemical Apparatus) July 2001, page 77 to 78" are arranged as the crystallization part, a belt filter as the solid liquid separation part and a crystal purification apparatus (KCP) described in "KAGAKU SOUCHI (Chemical Apparatus) July 2001, page 76 to 77" and JP-B-47-40621 as the crystal purification part is used The two crystallizers (1) and (2) composing the cation part are equipped with transverse model crystallization vessel and the inside of the crystallization vessel is partitioned with several cooling plates vertically against a horizontal plane. The cooling plates have a size by which gaps capable of passing solution can be formed at the lower part of the crystallization vessel and a stirring shaft equipped with stirring blades and a wiper for renewing cooling plane is penetrated at the center of respective cooling plates. Namely; the acrylic acid solution fed from the raw material solution-charging inlet that is provided at the edge part of the crystallization vessel is transferred to other edge part through the lower part of the cooling plates while being stirred by the stirring blades. At this time, the cooling and crystallization of the acrylic acid solution is carried out through the cooling plates.

When the acrylic acid solution is fed to the crystallizer (1), acrylic acid is crystallized at the crystallization vessel and after it is discharged together with crystallization mother liquid from the crystallizer (1), it is separated by crystals and residual mother liquid with a belt filter being the solid-liquid separation part. The crystallization mother liquid is fed to the crystallizer (2), further, acrylic acid is crystallized and crystals and the residual mother liquid are separated with the belt filter.

Then, crystals obtained in the crystallizers (1) and (2) are introduced into the crystal purification part.

Hereat, the crystal purification apparatus (KCP) described in "KAGAKU SOUCHI (Chemical Apparatus) July 2001, page 76 to 77" and JP-B-47-40621 is equipped with a screw conveyer at the center of a pipe made of metal (purification column) and equipped with a melting device to melt the crystals and a take-out orifice of a melted product at the top part of the purification column, and the take-out orifice of the residual solution (residual mother liquid) at the lower part of the purification column and the feed orifice of crystals at the lower side part of the column.

The crystals introduced in the crystal purification apparatus are conveyed to the upper part of the purification column by a belt conveyer with purified by sweating. The crystals conveyed to the upper part of the purification column are melted with a melting device and the greater portion of the melt of the crystals is taken out from the take-out orifice of a product. At this time, the portion of the melt of the crystals is dropped from the upper par of the purification column. The dropped melt of the crystals is brought in contact with crystals conveyed by a screw conveyer, rinses the surface of the crystals and finely taken out from the residue take-out orifice at the lower part of the purification column (residual mother liquid).

The amount of the dropped melt of the crystals may be suitably selected by the purity of objective acrylic acid, but is preferably 1 to 60% by mass of the amount of the melt of the crystals, more preferably 2 to 40% by mass and further preferably 5 to 35% by mass. Effect by sweating such as the rinsing of the crystals with the dropped melt is effectively obtained and the crystal purification column is stably operated. The residue (residual mother liquid) taken out from the lower part of the purification column may be recycled to the crystallization apparatus and/or crystallization residual mother liquid, but at least the portion is fed to the decomposition step (c) of the Michael adducts.

As the batch-wise crystallization apparatus, for example, a layer crystallization apparatus (dynamic crystallization apparatus) manufactured by Sulzer Chemtech GmbH, a static crystallization apparatus manufactured by BEFS PROKEM Inc. and the like may be used.

Hereat, concerning a case that the crystallization purification step (b2) is carried out at a batch-wise system, it is specifically illustrated referring a case of carrying out according to a multi-stage fractionation crystallization process as an example. Further, the crystallization purification step (b2) related to the present invention is not limited to this and may be carried out according to other crystallization processes.

The multi-stage fractionation crystallization process may be carried out by the dynamic crystallization step, or by combination of the dynamic crystallization step and the static crystallization step. The dynamic crystallization step is a step in which crystallization is carried out using dynamic crystallization apparatus having a tubular crystallization device equipped with temperature controlling mechanism for carrying out crystallization, sweating and melting, a tank collecting the mother liquid after sweating and a circulation pump feeding acrylic acid to the crystallization device, and the dynamic crystallization apparatus that can transfer acrylic acid solution from a storage device provided at the lower part of the crystallization device to the upper part of the crystallization device by the circulation pump. On the other hand, the static crystallization step is a step in which crystallization is carried out using a static crystallization apparatus which is a tubular crystallization device equipped with temperature controlling mechanism for carrying out crystallization, sweating and melting that has an extract valve at the lower part of the crystallization device and provided with a tank collecting the mother liquid after sweating.

Specifically, the crude acrylic acid-containing solution obtained in the absorption step is introduced to the crystallization device as liquid phase and acrylic acid in the liquid phase is coagulated on the cooling surface (tube wall surface). When the amount of the solid phase generated on the cooling surface is 40 to 90% by mass of the acrylic acid-containing solution introduced into the crystallization device and preferably 50 to 80% by mass, the liquid phase is immediately discharged from the crystallization device and the solid phase and liquid phase are separated. The discharge of the liquid phase may be either of a mode of pumping out (dynamic crystallization step) and a mode of flowing out from the crystallization device (static crystallization step).

On the other hand, after taking out the solid phase from the crystallization device, it may be fed to the purification step of carrying out rinsing or sweating in order to improve purity.

When the above-mentioned dynamic crystallization and static crystallization are carried out by the multi stage step, they may be advantageously carried out by adopting the principle of counter flow. In this case, substances crystallized in respective steps are separated from the mother liquid and fed to the following respective steps having further high purity. On the other hand, the residual mother liquid (crystallization residue) is fed to the following respective steps having further low purity.

Further, when the purity of acrylic acid is low, crystallization is difficult in the dynamic crystallization step, but the contact time with the cooling surface of the residual mother liquid is long in the static crystallization step in comparison with the dynamic crystallization step and the influence of temperature is easily transmitted; therefore even if the purity of acrylic acid is lowered, crystallization is easy. Accordingly, the final mother liquid of the dynamic crystallization step is fed to the static crystallization step in order to improve the collection rate of acrylic acid and crystallization may be further carried out.

The number of the crystallization stages may be suitably determined in accordance with purity required, but in order to obtain acrylic acid with high purity, the purification step (the dynamic crystallization step) is carried out 1 to 6 times, preferably 2 to 6 times and further preferably 2 to 4 times, and the stripping step (the dynamic crystallization step and/or the static crystallization step) is preferably carried out 0 to 5 times and more preferably 0 to 3 times. The entire steps by which acid with higher purity than a crude acid solution fed is obtained are usually known as the purification step and other entire steps are known as the stripping step. The stripping step is carried out for collecting acrylic acid in the mother liquid from the purification step. Further, the stripping step is not always provided and for example, when the high boiling point component separation step (b1) is employed, the above-mentioned stripping step may be abbreviated. The reason is that acrylic acid in the residual mother liquid is also collected in the high boiling point component separation step (b1).

Even if either of the above-mentioned dynamic crystallization step and static crystallization step is employed, the acrylic acid crystal obtained by the crystallization purification step (b2) may be used as a product as it is and further purification (rinsing, sweating and the like) is carried out if necessary, to be prepared as a product.

The residue (residual mother liquid) taken out from the crystallization purification step may be taken out to the outside of the system of acrylic acid production and a portion may be fed to the absorption step (a), but the present invention, at least one portion of the residual mother liquid is fed to the decomposition step (c) of the Michael adducts.

The operation conditions of the synthesis step of acrylic acid, the absorption step of acrylic acid gas, the azeotropic separation step and the purification step are not specifically limited and may be carried out while suitably adjusting, considering the composition of acrylic acid gas and the compositions of the acrylic acid-containing solution and the crude acrylic acid solution, etc.

[High Boiling Point Component Separation Step (b1)]

In the present invention, in addition to the above-mentioned steps, the high boiling point component separation step (b1) of separating the high boiling point components in the distillation column, the decomposition step (c) of decomposing the Michael adducts contained in the high boiling point components to generate acrylic acid, and the collection step (d) of collecting acrylic acid generated in the decomposition step are employed. The collection step (d) may be a step of capable of collecting acrylic acid generated in the decomposition step (c) and for example, the previous steps such as the absorption step (a), the purification step (b) and the like may be set as the collection step (d). Further, it is desirable that the high boiling point component separation step (b1) at the previous step is set as the collection step.

The high boiling point component separation step (b1) employed in the present invention may be included in the purification step (b). Further, the decomposition step (c) and the collection step (d) may be included in the purification step (b) and may be provided as a step different from the purification step (b). Further, as the preferable mode of the present invention, there is mentioned a mode in which acrylic acid is collected by providing the high boiling point component containing solution (which is obtained after the high boiling point component separation step (b1)) that is separated from acrylic acid as a desired product, and discharged in the purification step (b), to the decomposition step (c) and the collection step (d).

Figure 2:
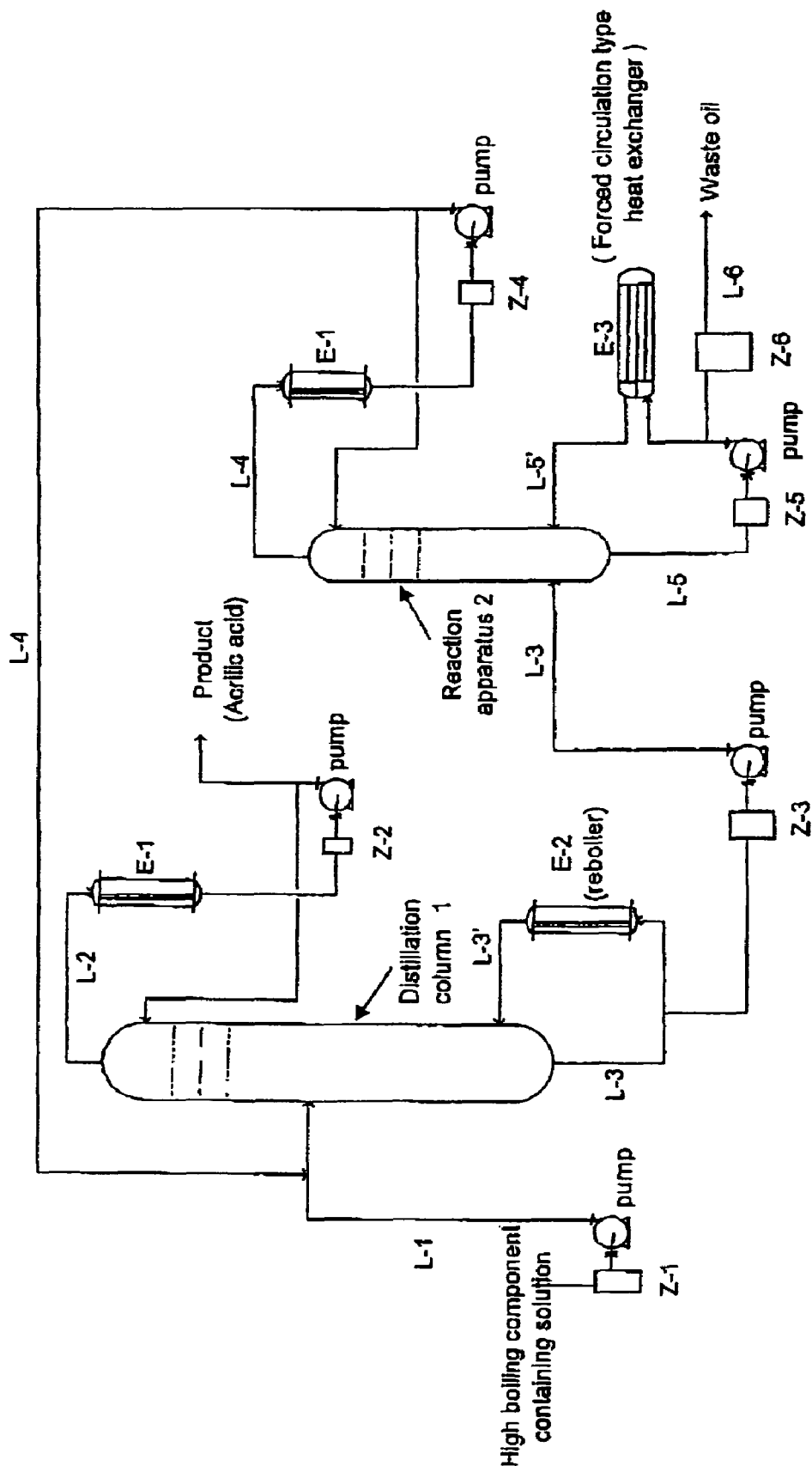
FIG. 2 is a step diagram showing other example of the step of the process for producing acrylic acid related to the present invention.

Then, the preferable mode of the present invention is specifically illustrated while referring to the process shown in FIG. 2.

The high boiling point component containing solution that is fed to the purification step (b) (not illustrated) through the synthesis step and the absorption step (a) and separated from acrylic acid in the purification step is fed to the distillation column 1 (high boiling point component separation column) through the line L-1 that separates the high boiling point components (the high boiling point component separation step (b1)).

The high boiling point component separation step may be either a step of separating acrylic acid from the high boiling point components at the purification step (not illustrated) and may be a step of separating acrylic acid and other low-boiling point component from the high boiling point component which is contained in the high boiling point component containing solution obtained by separating acrylic acid in the purification step. The acrylic acid separated is distilled from the top of the distillation column 1, condensed at the condenser E-1 through the line L-2, and then collected as a product or for feeding it to further purification step and the like. Further, the portion of acrylic acid and the low-boiling point component introduced into the line L-2 may be recycled to the distillation column 1 and used as a reflux liquid.

On the other hand, the bottom solution (the high boiling point components) of the distillation column 1 is fed to the reaction-distillation apparatus 2 (the distillation column) (the decomposition step (c)) through the line L-3. Further, all of the high boiling point components introduced in the line L-3 may be fed to the next step, but a portion may pass the heat source E-2 on the line L-3 and then may be recycled again to the distillation column 1. Further, insoluble components contained in the distillate or the bottom solution of the distillation column 1 may be removed from the distillate distilled off from the distillation column 1 and the bottom solution discharged from the distillation column 1, through the strainer Z-3 before being fed to the next step.

Hereat, the high boiling point components mean a by-product at the production of acrylic acid or the starting raw material and contain components with higher boiling point than acrylic acid at the standard state. The specific high boiling point components include the Michael adducts (the dimer of acrylic acid and the like), furfural protoanemonin, maleic acid, maleic anhydride and the like.

As apparatus that may be used as the distillation column (the high boiling point component separation column) of the high boiling point component separation step (b1), a packed column, a shelf plate column (tray column) and the like are mentioned. As the filling material filled in the packed column, any one of those exemplified as filling materials in the decomposition step described later may be used. Further, trays exemplified in the decomposition step described later may be used for the tray provided in the shelf plate column. Needless to say, the filing materials and trays are may be used in combination. Further, the shelf plate column is preferably used from the viewpoint of reducing the contamination of maleic acid into the distillate (acrylic acid). At this time, the number of theoretical stage of the shelf plate column is preferably 2 to 20 stages and more preferably 4 to 12 stages. The reflux ratio is preferably 0.2 to 4 and more preferably 0.4 to 2.

The operation condition of the distillation column (the high boiling point component separation column) may be condition by which acrylic acid can be separated from the high boiling point components and may be suitably selected the acrylic acid concentration of the high boiling point components (crude acrylic acid solution) introduced, water concentration, acetic acid concentration and the like. For example, the temperature of the bottom of the high boiling point component separation column is preferably 90° C. or more, more preferably 95° C. or more and preferably 130° C. or less, more preferably 125° C. or less and further preferably 120° C. or less. On the other hand, the temperature of the top of the high boiling point component separation column (distillation column) is preferably 40 to 90° C. usually and more preferably 50 to 80° C. Further, the residential time of the bottom solution of the high boiling point component separation column is preferably 2 to 30 hours and more preferably 4 to 25 hours. Further, the ratio "F/B" (hereinafter, F/B is called as condensation magnification) which represents the ratio of the amount the solution fed to the distillation column (F) to the amount of the extract solution (bottom solution) from the distillation column (B) is preferably 5 to 20 and more preferably 8 to 15. Further, the column top pressure of the high boiling point component separation column (absolute pressure) is preferably 1.0 to 40 kPa, more preferably 1.5 to 30 kPa and further preferably 2.0 to 20 kPa. When the column top pressure of the high boiling point component separation column is within the above-mentioned range, the large sizing of the distillation column and a condenser and a vacuum apparatus provided on the distillation column is also unnecessary and there is also little fear that acrylic acid is polymerized.

As the heat source E-2 of the distillation column 1 (the high boiling point component separation column), heat exchangers such as a multi tube type heat exchanger, a plate type heat exchanger, a spiral type heat exchanger, a forced circulation type heat exchanger and a thin film type heat exchanger, and a reboiler may be used.

Further, a polymerization inhibitor may be added to the reflux liquid in order to prevent the polymerization of polymerizable substances such as acrylic acid at distillation. The polymerization inhibitor includes one or more of compounds selected from the group consisting of an N-oxyl compound, a phenol compound, a manganese salt such as manganese acetate, a copper salt of dialkyldithiocarbamate such as copper dibutylthiocarbamate, a nitroso compound, an amine compound and phenothiazine that are described in JP-A-2001-348360, JP-A-2001-348358, JP-A-2001-348359 and the like.

The distillate obtained in the high boiling point component separation step may be used as a product (acrylic acid) and may be also fed to the further purification step. Needless to say, the distillate from the distillation column (the high boiling point component separation column) may be fed to the absorption step (a) which is the upstream side step of the high boiling point component separation step (b1) and the purification step (b) such as the azeotropic dehydration step, as the acrylic acid containing solution (collection).

On the other hand, the bottom solution of the distillation column 1 (the high boiling point component separation column) is fed to the reaction-distillation apparatus 2 (the reaction-distillation column) through the line L-3 and decomposes valuable articles contained in the bottom solution of the distillation column to prepare acrylic acid (the decomposition step (c)).

Further, in the present invention process, when the total amount of maleic acid and maleic anhydride contained in the high boiling point components fed to the decomposition step (c) is set as 100% by mass, the proportion of the amount of maleic acid is set as 70% or less. The entire maleic acid concentration at this time (the total concentration of maleic acid and maleic anhydride) is preferably 3 to 25% by mass in 100% by mass of solution fed to the decomposition step (the high boiling point component containing solution). It is more preferably 5 to 20% by mass and further preferably 7 to 14% by mass.

Further, the concentration (base on 100% by weight of the high boiling point component containing solution) of the Michael adducts contained in the high boiling point components fed to the decomposition step (c) is preferably 20 to 60% by mass. It is more preferably 25 to 55% by mass and further 30 to 50% by mass. Further, operation conditions such as the column bottom temperature of the distillation column in the high boiling point component separation step (b1), the residence time, the number of theoretical stages of the distillation apparatus used and the reflux ratio may be controlled as described above, so that the maleic acid amount in the high boiling point components is set as the above-mentioned range. Further, the water-including maleic acid amount in the high boiling point components fed to the distillation column and the amount of the Michael adducts may be adjusted by controlling conditions such as the decomposition (column bottom) temperature of the decomposition step (c) described later, the residence time, condensation magnification, reflux ratio and column internal temperature and using the distillate (recycle solution) from the decomposition step (c).

Thus, it is the preferable embodiment of the present invention that the amount of the Michael adducts is adjusted at a specific range, in addition to adjustment of the amount of maleic acid contained in the high boiling component containing solution. Thereby, problems such as the blockage of piping derived from maleic acid, adhered matters and the rise of the viscosity of waste oil in the decomposition step (c) described later, are further reduced.

In the high boiling point component separation step (b1), acrylic acid is also collected in addition to the separation of the high boiling point component. Consequently, when the high boiling point component separation step (b1) is employed, the stripping step of the crystallization purification step (b2) may be abbreviated when crystallization purification is carried out as the purification step (b) and the production step of acrylic acid becomes more convenient. Further, since the distillate circulating from the high boiling point component separation step (b1) to the absorption step (a) reduces adequately the high boiling point components such as maleic acid that have fear of polymerization by heating, the yield of acrylic acid is improved without damaging the operation property of the absorption step (a).

[Decomposition Step (c)]

In the high boiling point component separation step (b1), the high boiling point components extracted from the bottom part of the distillation column 1 (the high boiling point component separation column) is fed to the reaction-distillation apparatus 2 (the reaction-distillation column 2) that carries out the decomposition of the Michael adducts, through the line L-3. The high boiling point components include the Michael adducts such as the dimer of acrylic acid, the trimer of acrylic acid and acrylic acid oligomer, but the Michael adducts may be collected as acrylic acid by decomposing the Michael adducts. Namely, the decomposition step related to the present invention is a step in which the high boiling point components are heated and valuable matters such as the Michael adducts contained in the high boiling point components are decomposed to generate acrylic acid (the decomposition step (c)).

As shown in FIG. 2, it is preferable that acrylic acid generated in the reaction-distillation apparatus 2 is distilled off from the column top of the reaction-distillation apparatus 2 and circulated to the distillation column 1 through the line L-4 and the line L-1 connected with the distillation column 1 (the high boiling point component separation column), or from the line L-4 directly (not illustrated). On the other hand, the residual solution of the reaction-distillation apparatus 2 is discharged out of the acrylic acid production system through the lines L-5 and L-6. Needless to say, the portion of the residual solution may be circulated to the heat exchanger E-3 to be returned to the reaction distillation apparatus 2. Further, FIG. 2 shows an example in which a forced circulation type heat exchanger is used as the heat exchanger.

It is preferable to employ a decomposition process that secure adequate residence time for treating decomposition objects in order to efficiently decompose the Michael adducts in the decomposition step. In the present invention, as the decomposition step (c), the reaction-distillation process that carry out the decomposition of the Michael adducts and the evaporation or distillation of decomposed products simultaneously (acrylic acid) is preferably adopted. Hereat, the reaction-distillation process means a process of distilling the decomposed products by evaporation while decomposing the Michael adducts. The reaction by which the Michael adducts are generated from acrylic acid is equilibrium reaction. Accordingly, when the reaction distillation process is employed and acrylic acid which is a decomposed product is distilled off by evaporation at the same time with the decomposition reaction of the Michael adducts, the decomposition reaction is accelerated because the distillation of decomposed product (acrylic acid) shifts the equilibrium in favor of the generation of acrylic acid and the efficient decomposition of the Michael adducts is carried out.

The embodiment of the above-mentioned reaction distillation is not limited and may be carried out by any one of a batch type, a semi-continuous type and a continuous type, but the continuous type is preferable. Further, the form of a reaction apparatus is not specifically limited, and general reaction distillation apparatuses such as simple reactors such as a pot still, a distillation column and a packed column; a distillation column (plate type distillation column) provided with trays (stage plate) on the reactor; an apparatus combining a reactor with the distillation column; and a reactor provided with a stirrer may be used.

The general reaction-distillation apparatus means a reaction-distillation apparatus that can decompose the Michael adducts by the reaction-distillation process and can secure adequate residence time. As described later, as the heat source of the reaction distillation apparatus, conventionally known heat sources may be employed but it is preferable to employ a forced circulation type heat exchanger from the viewpoint of securing adequate residence time. Since the forced circulation type heat exchanger provide adequate heat quantity to an objective decomposing solution and circulate the objective decomposing solution in the reaction-distillation apparatus, adequate residence time is obtained in the reaction apparatus. Consequently, the forced circulation type heat exchanger is very suitable as a heat source at decomposing the Michael adducts by the reaction-distillation process. Further, when the forced circulation type heat exchanger is used, the objective decomposing solution is rapidly circulated in the reaction distillation apparatus; therefore excessive heat is hardly transmitted to waste oil and problems such as generating polymer and adhering stain on the apparatus, may be reduced. Accordingly, decomposition operation carried out for a long period stably.

Further, the forced circulation type heat exchanger may be used in combination with a thin-film evaporator. The thin-film evaporator is preferable as a heat source, but it is slightly inferior in efficiency for a point of providing adequate heat quantity and residence time to the objective decomposing article and rapidly decomposing it; therefore it is required to be carefully and resourcefully used. Consequently, when the thin-film evaporator is used as a heat source, the forced circulation type heat exchanger is preferably used in combination.

Further, the plate type distillation column is preferably employed from the viewpoints of preventing stain in the distillation column and efficiently separating by-products having boiling point near to acrylic acid for example, benzaldehyde, furfural and the like). At this time, the number of theoretical stage is preferably 2 stages or more, more preferably 3 stages or more and preferably 15 stages or less and more preferably 10 stages or less. The reflux ratio is preferably 0.5 to 6 and more preferably 0.7 to 4. Since the flow-out of furfural and benzaldehyde may be suppressed by adjusting the number of theoretical stage and the reflux ratio as the above-mentioned range, the quality of the product is kept good. Further, since the condensation and precipitation of maleic acid in the column and the generation of a copolymer with acrylic acid are further suppressed by controlling composition in the column (the composition of solution retained on plates in the column) and liquid depth per one tray, troubles such as stain and the raise of pressure loss in the column and the increase of utilities such as operation cost are suppressed. In case that the distillate is fed to the previous steps such as the synthesis step and absorption step (a) as circulation solution, if the circulation solution contains maleic acid, the maleic add may come to contain water in the step again because water exists in the previous step. In such case, the amount of water-including maleic acid in feed solution to the decomposition step may be increased. Consequently, it is desirable that maleic acid concentration in the distillate is reduced as low as possible for further reducing the amount of the water-including maleic acid in the feed solution to the decomposition step; therefore it is preferable that the number of theoretical stage and reflux ratio are set as the above-mentioned range.

The example of the shelf plate (tray) provided in the decomposition reaction apparatus includes a bubble-cap tray, a uniflat tray, a perforated tray, a jet tray, a bubble tray, cross flow contact using a venturi tray, a turbo grid tray, a dual flow tray, a ripple tray, a Kittel tray and the like. It is preferable to employ the tray having opening with a hole diameter of 10 to 50 mm (more preferably 12 to 30 mm) from the viewpoint of preventing the condensation and precipitation of acrylic acid and the accumulation of copolymers with acrylic acid in the column. Further, the tray and filling materials may be used in combination.

The filling materials are preferably those that are equipped with durability for pressurization and high temperature and are hardly reacted with components in the residual mother liquid. From the viewpoint, a filling material made of metal such as alumina and stainless is recommended. Further, the shapes of the filling materials are preferably those hardly raising the pressure loss of the reaction-distillation apparatus. The filling materials include known Raschig rings, Lessing rings, poll rings, flexy rings, cascade mini rings (manufactured by Dotwell Inc.), Raschig super rings, Interlocks Metal Tower Packing (manufactured by Norton Inc.) and Interlocks Saddle (manufactured by Norton Inc.), filling materials described in "KAGAKU KOUGAKU BINRAN (Chemical Engineering Handbook)" (edited by Chemical Engineering Academy, 6$^{th}$ Edition, page 604, FIGS. 11 and 13), Mellapak (manufactured by Sumitomo Heavy Industries Ltd), Jempak (manufactured by Chiyoda Corporation), Techno-Pack (manufactured by Sanrei Techno Corporation), Montz-Pak (manufactured by Montz GmbH, Interlocks High Performance Structured Packing (manufactured by Norton Co.) and other metal plate type regular filling materials described in "KAGAKU KOU- GAKU BINRAN (Chemical Engineering Handbook)" (edited by Chemical Engineering Academy, 6th Edition) page 567.

Among the filling materials, Raschig rings, Lessing rings, poll rings, flexy rings, cascade mini rings, Raschig super rings, Interlocks Metal Tower Packing and Interlocks Saddle are preferable because the surface area per 1 m$^3$ and void ratio of the filling material is high, substance exchange is efficiently carried out and pressure loss is reduced. Cascade mini rings are most preferable.

As the reaction apparatus, when the shelf plate distillation column is employed, the position of 70 to 100% of the total number of theoretical stage in which column top side is as a base point is preferably heated at 125° C. or less, 90 to 120° C. is more preferable and 95 to 115° C. is further preferable. Further, the "the position of 70 to 100% of the total number of theoretical stage in which column top side is as a base point" means that when the column top is calculated as the first stage, the position is either of positions of 70 to 100% of the total number of theoretical stage and corresponds to the lower position of the height direction of the shelf plate distillation column. Since the position corresponds to a position at which reaction solution (the high boiling point components) heated at the heat exchanger is fed, it is said as the position at which temperature is easily raised in the distillation apparatus and is said one of spots at which the precipitation of the water-including maleic acid by the condensation of maleic acid and the generation of a copolymer of the water-including maleic acid with acrylic acid occur easily. Further, when the temperature of the position is too low, it may be hard to proceed the decomposition reaction of the Michael adducts. Accordingly, the generation of polymers may be suppressed and the decomposition reaction of the Michael adducts proceeds more smoothly by setting the temperature of the position of 70 to 100% of the total number of theoretical stage in which column top side is a base point as the above-mentioned range.

The residence time (based on extract solution which is discharged from the bottom of the reaction-distillation column) of the reaction solution (high boiling component) in the reaction apparatus may be suitably set in accordance with the temperature of column bottom, but for example, 0.2 to 30 hours is preferable, 0.5 to 15 hours is more preferable and 1 to 10 hours is further preferable. When the temperature is too high, or when the residence time is too long, the decomposition reaction proceeds but the property of the reaction solution is likely to deteriorate, and increasing viscosity and adhering stain may occur in the inside of the reaction apparatus. On the other hand, when the temperature is too low, or when the residence time is too short, it may occur that the Michael adducts are hardly decomposed adequately. Further, when the azeotropic dehydration step is employed or the crystallization purification process is employed as the purification step, maleic acid in the high boiling point components (or residual mother liquid) exists often as the water-including maleic acid and troubles such as precipitation occur easily; therefore the Michael adducts is decomposed further efficiently and without deteriorating the property of the reaction solution when it is heated to the temperature at which the decomposition reaction of the Michael adducts reaches rapidly at equilibrium in like manner as the above-mentioned condition and the residence time is shortened.

As the heat source E-3 of the reaction-distillation apparatus, a multi tube type heat exchanger, a plate type heat exchanger, a spiral type heat exchanger, a forced circulation type heat exchanger, a thin-film evaporator, a reboiler and the like may be used. These may be used alone or 2 or more may be used in combination. Further, when the thin-film evaporator is used, it is preferable that it is used in combination with other heat source. In particular, when the viscosity of decomposing objective is high and the column bottom portion of the reaction apparatus is required to be kept at high temperature, the forced circulation type heat exchanger is preferably employed among the above mentioned heat exchangers. The forced circulation type heat exchanger is equipped with a pump for circulation, and since it adopts a constitution that the portion of the column bottom solution in the reaction apparatus is continuously taken out to be returned to the reaction apparatus, the generation and adherence of polymers and precipitated matters in the reaction apparatus is reduced in comparison with a case of heating through the wall surface in the reaction apparatus. Further, the residence time in the reaction-distillation apparatus is adequately secured. Accordingly, even if the viscosity of the residual mother liquid is high, the decomposition reaction of the Michael adducts may be carried out stably for a long period. As described in JP-A-H09-110778, the forced circulation type heat exchanger may be a heat exchanger in which a diaphragm structure is provided in some part of piping. The heat exchanger having such constitution keeps the super heat state of liquid and efficiently provides energy necessary for boiling and evaporation in the reaction apparatus. Further, since troubles by staining and the deterioration of property are suppressed, the decomposition reaction is rapidly carried out.

When the forced circulation type heat exchanger is used, operation is preferably carried out at a decomposition temperature of 155 to 220° C. and more preferably 160 to 200° C. At this time, the temperature of the heat source of the forced circulation type heat exchanger is preferably adjusted so that difference between the decomposition temperature (column bottom temperature) and the temperature of the heat source is 15 to 80° C. and the difference is recommended to be more preferably 20 to 60° C. Since the deterioration of properties such as the adherence of stain on the heat exchanger and the rise of oil viscosity may be suppressed by setting the difference between the decomposition temperature (column bottom temperature) and the heating temperature as above-mentioned range, it is more preferable that the difference between the decomposition temperature (column bottom temperature) and the heating temperature is within the range. Further, it is recommended that the circulation amount of the column bottom solution in the forced circulation type heat exchanger is preferably 100 to 300 m$^3$/h and more preferably 140 to 250 m$^3$/h. Since adequate heat efficiency is obtained and the adherence of stain on the heat exchanger may be suppressed by setting the circulation amount as the range, it is preferable for stable operation for a long period.

Further, the collision plate of liquid droplet and the like may be provided in the apparatus for reducing troubles such as staining in the reaction apparatus and the deterioration of liquid properties. Thus, since droplets from liquid surface are cut when feed solution is fed in the distillation column (the reaction-distillation apparatus), troubles derived from the generation of polymers and precipitates at the upper side of the collision plate may be reduced.

As pressure at the decomposition reaction, there is preferably adopted pressure at which acrylic acid generated by the decomposition reaction and the greater part of useful components such as acrylic acid contained in the feed solution which is the raw material of the decomposition reaction may be evaporated and the decomposition of the Michael adducts which is equilibrium reaction proceeds rapidly. For example, the column top pressure (gauge pressure) of the reaction apparatus is preferably 6.7 to 64 kPa (50 to 480 torr) and more preferably 13.3 to 40 kPa (100 to 300 torr). Twenty to 33.3 kPa (150 to 250 torr) is further preferably recommended (operational pressure). The column top temperature is preferably 60 to 150° C. and more preferably 80 to 130° C. Ninety to 120° C. is further preferably recommended. Since it may be suppressed that the high boiling point components in by-products, protoanemonin, furfural with boiling point near to that of acrylic acid, benzaldehyde and the like are distilled together with acrylic acid by setting the column top temperature and the column top pressure as the above mentioned range, the quality of the product is kept good even if the distillate of the decomposition step (c) is fed to the absorption column (the absorption step (a)) of acrylic acid-containing gas and the high boiling point component separation column (the high boiling point component separation step (b1)). Further, since high temperature is not required for the decomposition reaction of the Michael adducts comparing to the case of too high column top temperature and too high column top pressure, neither the deterioration of properties of the reaction solution nor the lowering of decomposition rate hardly occur.

In the decomposition step (c), one or more catalysts selected from Lewis acid, Lewis base, inorganic acids such as sulfuric acid and phosphoric acid, alkali metal, alkali earth metal, organic acids such as methane sulfonic acid and p-toluene sulfonic acid, N-oxyl compounds, amines and the like may be used as a decomposition catalyst in order to promote the decomposition of the Michael adducts. Among the above-mentioned decomposition catalysts, the N-oxyl compound is preferably used. The reason is that when the N-oxyl compound is contained in the circulation solution that circulates distillate distilled from the decomposition step, namely, the reaction-distillation column (the reaction-distillation apparatus) to other steps, for example, the absorption step of acrylic acid-containing gas and the high boiling point component separation step (the high boiling point component separation column 1), it may also act as the polymerization inhibitor of acrylic acid.

The addition amount of the catalyst is preferably 0.05 to 3% by mass based on the column bottom solution of the reaction apparatus and more preferably 0.1 to 1% by mass. Further, the catalyst is enough to exist at decomposition and the addition timing of the catalyst is not limited to only the decomposition step. For example, it may be added when the high boiling point component containing solution is fed to the reaction apparatus used in the decomposition step, in addition to the absorption column at the acrylic acid absorption step and various distillation columns used at respective step.

[Collection Step (d)]

Acrylic acid generated by the decomposition of the Michael adducts in the decomposition step (c) is distilled off from the column top side of the reaction-distillation apparatus 2 (the decomposition step) and delivered to the acrylic acid absorption step (not illustrated) and the high boiling point component separation column (the distillation column 1, the high boiling point component separation step (b1)) through the line L-4 and collected at respective step. At this time, the concentration of maleic acid in the distillate extracted from the column top side of the reaction-distillation apparatus 2 is preferable as low as possible, but it is preferably 2.0% by mass or less, more preferably 1.8% by mass or less, further preferably 1.5% by mass or less and further more preferably 0.6% by mass or less. Thereby, since the condensation trouble of acrylic acid derived from the distillate discharged from the reaction-distillation apparatus 2 is reduced, the reduction of the amount of the water-including maleic acid contained in the feed solution from the high boiling point component separation column (the distillation column 1) of the previous step becomes easy. In order to reduce the concentration of maleic acid in the distillate, for example, it is preferable that the number of theoretical stage of the reactor used as the reaction apparatus and the operation condition such as reflux ratio are set as the above-mentioned range. Further, the content of the Michael adducts in the distillate is preferably 0.3% by mass or less and more preferably 0.2% by mass or less.

Further, oxygen or gas containing oxygen may be added to the distillate distilled from the reaction distillation apparatus 2 in order to prevent the polymerization of acrylic acid contained in the distillate. The gas containing oxygen is introduced in the gas phase part or liquid phase part of the reaction-distillation apparatus 2.

The gas containing oxygen includes pure oxygen, mixed gas obtained by diluting oxygen with inactive gas (nitrogen and the like), air and the like. The addition amount is preferably set so that oxygen concentration is 0.01 to 5% by mass based on gas volume distilled from the column top side of the reaction-distillation apparatus 2, more preferably 0.02 to 3% by mass and further preferably 0.05 to 1% by mass. When oxygen concentration in the distillate is within the above-mentioned range, the effect of preventing polymerization is adequately obtained. Further, the amount of an active substance such as acrylic acid discharged to outside of the acrylic acid production system accompanied with oxygen or gas containing oxygen is suppressed at low level and the pressure control of the decomposition step becomes easy.

As described above, the process for producing acrylic acid of the present invention provides the high boiling point component separation step (b1) that separates the high boiling point components in the feed solution fed to the decomposition step (c), as the previous step of the decomposition step (c), feeds the high boiling point components separated in the high boiling point component separation step (b1) to the decomposition step (c), and feeds acrylic acid generated by the decomposition of the Michael adducts at the decomposition step (c) to the absorption step (a), the high boiling point component separation step (b1) and the like, to be collected (the collection step (d)).

Namely, all of the distillate from the decomposition step (c) may be fed to the absorption step (a) through the high boiling point component separation step (b1) (FIG. 1, the reaction-distillation apparatus 2→line L-11'→line L-11→the absorption column 3), or a portion of the distillate from the decomposition step (c) is fed to the absorption step (a) through the high boiling point component separation step (b1) (the reaction-distillation apparatus 2→line L-4→the distillation column 1→line L-11→the absorption column 3), and the residual portion may be fed to the absorption step (a) through the line L-11' without passing through the high boiling point component separation step (b1) (the reaction-distillation apparatus 2→the line L-11'→the line L-11→the absorption column 3). A mode that all of the distillate obtained in the decomposition step (c) is fed to the absorption step (a) through the high boiling point component separation step (b1) is more preferable (modes of FIGS. 2 and 3, however, the absorption column is not illustrated).

The efficiency of the step for producing acrylic acid may be further improved by adoption of the above mentioned preferable mode. Namely, when the high boiling point component separation step (b1) is provided as the previous step of the decomposition step (c), the collection of acrylic acid may be carried out together with the separation of the high boiling point components in the high boiling point component separation step (b1) and the successive decomposition step (c) and the like without setting excessively severe separation condition in the purification step (b) such as crystallization purification and distillation purification. Further, the decomposition of the Michael adducts is also smoothly carried out. Further, when the distillate of the decomposition step (c) is fed to the absorption step (a) through the high boiling point component separation step (b1), undesirable components, in particular, maleic acid that leads to problems such as precipitation and impurities such as furfural and benzaldehyde that are hardly separated by crystallization purification are reduced in the high boiling point component separation step (b1); therefore load to the purification step (b) may be reduced.

Further, even if the purification step (b) is carried out under operation condition most advantageous for purification operation, the collection of acrylic acid that was not separated at the purification step (b) (the crystallization purification step (b2) and the like) is collected at the successive high boiling point component separation step (b1), by adopting the above-mentioned mode. Further, since acrylic acid generated by the decomposition of the Michael adducts contained in the high boiling point components in the decomposition step (c) is collected through the high boiling point component separation step (b1), the yield of acrylic acid is also improved.

Thus, in the present invention, while the respective steps perform respective roles, the respective steps are mutually linked organically at complementary relation; therefore the production efficiency of acrylic acid is further improved.

Figure 4:
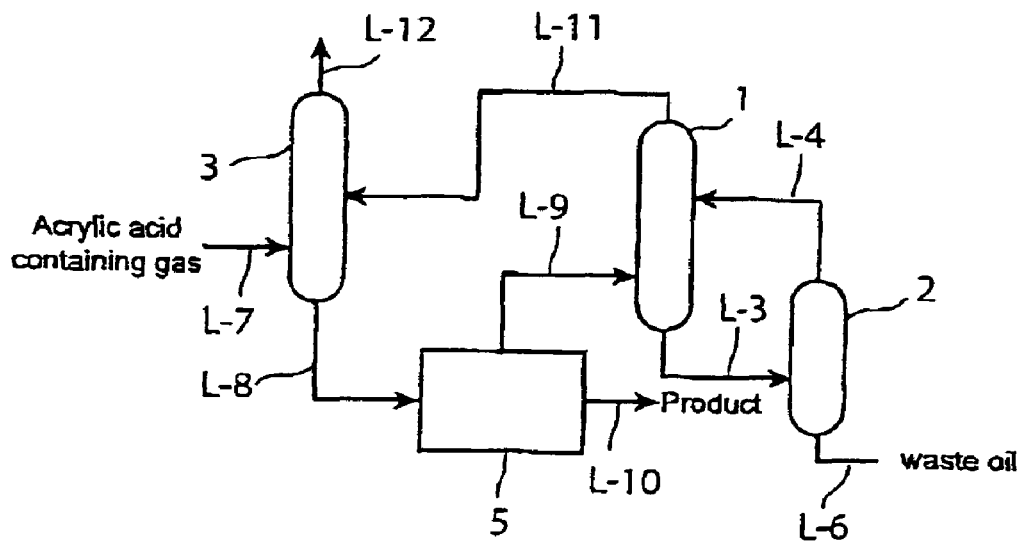
FIG. 4 is a step diagram showing other example of the step of the process for producing acrylic acid related to the present invention.

The preferable mode of the present invention described above is specifically illustrated below, exemplifying the process shown in FIG. 4.

Firstly, acrylic acid-containing solution obtained in the acrylic acid absorption column 3 is fed to the purification apparatus 5 through the line L-7 and acrylic acid as the product is taken out from the purification apparatus 5 through the line L-10. On the other hand, components separated from acrylic acid at the purification apparatus 5 are discharged from the purification apparatus 5 and fed to the distillation column 1 (the high boiling point component separation column) through the line L-9. The high boiling point component containing solution is heated at the distillation column 1, the distillate (containing acrylic acid and low boiling point component) is distilled off from the column top of the distillation column 1 and circulated to the absorption column 3 through the line L-11. On the other hand, the column bottom solution containing the Michael adducts and the high boiling point components are fed to the reaction-distillation apparatus 2 through the line L-3 (the decomposition step (c)). Acrylic acid generated in the reaction-distillation apparatus 2 is circulated to the distillation column 1 through the line L-4, fed together with other low boiling point component distilled off from the distillation column 1 to the absorption column 3 through the line L-11 and collected as acrylic acid solution. Further, the residual solution of the reaction-distillation apparatus 2 is discharged through the line L-6.

EXAMPLES

The present invention is specifically described below based on Examples. However, the under-mentioned Examples do not limit the present invention and all of modifications within the scope not deviating the purport of the fore-mention and the post-mention is included in the technical range of the present invention. Evaluation methods performed in the examples are as follows.

[Proportion of the Amount Maleic Acid]

In the present Example, the proportion of the amount of maleic acid to a sum of the maleic acid and maleic anhydride in the high boiling point components fed from the high boiling point component separation step to the decomposition step was calculated by measuring the masses of maleic acid and maleic anhydride contained in the column bottom solution of the high boiling point separation column, substituting values obtained into the under-mentioned equation (1) to obtain the proportion of the amount of maleic acid.

The mass of maleic acid was obtained by reacting maleic acid contained in the column bottom solution with methanol, measuring the mass of the generated monomethyl maleic acid by gas chromatography and converting the obtained value to the mass of maleic acid. In addition, at this time, maleic anhydride is not reacted with methanol.

On the other hand, the mass of maleic anhydride was obtained by measuring the total mass of maleic acid and maleic anhydride contained in the column bottom solution by liquid chromatography and then subtracting the mass of maleic acid from the total mass of maleic acid and maleic anhydride to calculate the mass of maleic anhydride.

[Equation 1]

$$\frac{[\text{Maleic acid (mass)}]}{[\text{Maleic acid (mass)}] + [\text{Maleic anhydride (mass)}]} \times 100 \leq 70\% \quad (1)$$

[Conversion Rate]

The mass of the high boiling point component containing solution fed to the decomposition step and the mass of the Michael adducts contained in the distillate after the decomposition step were measured by gas chromatography and the conversion rate of the Michael adducts was calculated by the under-mentioned equation (2).

[Equation 2]

$$\text{Conversion (\%)} = \frac{\text{Mass of Michael adducts decomposed}}{\text{Mass of Michael adducts before decomposition}} \times 100 \quad (2)$$

[Selectivity]

The mass of the Michael adducts, the mass of acrylic acid in the high boiling point component containing solution fed to the decomposition step and the mass of acrylic acid contained in the distillate after the decomposition step were measured by gas chromatography and the selectivity of the decomposition reaction was calculated by the under-mentioned equation (3).

[Equation 3]

$$\text{Selectivity (\%)} = \frac{\text{Mass of acrylic acid generated}}{\text{Mass of Michael adducts before decomposition}} \times 100 \quad (3)$$

[Synthesis of Acrylic Acid]

Acrylic acid-containing gas obtained by the propylene catalytic gas phase oxidation process was brought in contact with a absorption solvent to be absorbed as crude acrylic acid-containing solution (absorption step) and then, low boiling point components were removed from the crude acrylic acid-containing solution obtained at the azeotropic separation step to obtain crude acrylic acid-containing solution containing the high boiling point component. The composition of the crude acrylic acid-containing solution obtained was acrylic acid: 96.05% by mass, maleic acid: 0.49% by mass, maleic anhydride. 0.33% by mass, acrylic acid dimer (the Michael adduct): 3% by mass, furfural: 0.03% by mass, benzaldehyde: 0.03% by mass, protoanemonin: 0.02% by mass and water: 0.05% by mass.

Experimental Example 1-1

The collection of acrylic acid was carried out according to the step diagram shown in FIG. 2. Further, in Experimental Example 1-1, a high boiling point separation column (the number of stage: 50 stages, sieve tray distillation column) was used as the distillation column 1 of the high boiling point component separation step, and a reaction-distillation column with tray (the number of stage: 20 stages, sieve tray distillation column 2) was used as the reaction-distillation apparatus 2 of the decomposition step. Further, as the heat exchanger of the decomposition step, a forced circulation type heat exchanger ("E-3" in FIG. 1) was used and when respective feed solutions were fed to the high boiling point separation column and the reaction distillation column, they were fed after removing impurities in the solutions through strainers (Z-1 to Z-6). The decomposition temperature (the column bottom temperature of the reaction distillation column) of the decomposition step at this time was 170° C., the temperature of the position of 80% ($16^{th}$ stage among 20 theoretical stages) of the total number of theoretical stage of the reaction distillation column was 120° C. and a reflux ratio was 4. Further, the temperature of the heat source of the forced circulation type heat exchanger was 220° C. and temperature difference ($\Delta T$) between decomposition temperature and the heat source of the forced circulation type heat exchanger was 50° C.

Firstly, the crude acrylic acid-containing solution obtained by the above-mentioned synthesis of acrylic acid was introduced into the distillation column 1 (the high boiling point separation column) together with the distillate from the decomposition step described later. The distillation column 1 was controlled at operation pressure: 46.7 hPa (35 mmhg) and column bottom temperature: 98° C. and operated at a reflux ratio: 0.9 and the residence time of the distillate: 5 hours, and acrylic acid and other low boiling point component were distilled from the column top to obtain the high boiling point component-containing solution (the high boiling point components) containing the Michael adducts from the column bottom of the distillation column 1. Further, the proportion (the proportion of the amount of maleic acid calculated from the above-mentioned equation (1) is also similar to Experimental Examples below) of the amount of maleic acid contained in the high boiling point component-containing solution was 38%. Further, the Michael adducts were contained by 42% by mass.

Then, the high boiling point component-containing solution obtained was introduced into the reaction-distillation apparatus 2 (the reaction-distillation column with tray) at 10 kg/hr and the Michael adducts were decomposed to be collected. The operation condition of the reaction distillation apparatus 2 (the decomposition step) and the result are shown in Table 1.

The decomposition operation of the Michael adducts was continued for two weeks, but troubles such as the generation of stain in the reaction apparatus and pressure rise in the apparatus were not occurred, the viscosity of waste oil (the column bottom solution of the reaction distillation apparatus 2) was also low and the decomposition of the Michael adducts was stably carried out. Further, the viscosity of the waste oil was measured at constant temperature (100° C.) using a vibration type viscometer.

The conversion of the Michael adducts at this time was 85% and the yield of acrylic acid for the Michael adducts fed was 83.3%

Experimental Example 1-2

The collection of acrylic acid was carried out in like manner as Experimental Example 1-1 except that the residual mother liquid of the crystallization step obtained by carrying out crystallization purification successive to the absorption step in the above-mentioned synthesis of acrylic acid was used as the high boiling point component-containing solution fed to the distillation column 1 (the high boiling point separation column). The composition of the crude acrylic acid-containing solution obtained at this time was acrylic acid: 87.1% by mass, maleic acid: 0.72% by mass, maleic anhydride: 0.1% by mass, acrylic acid dimer (the Michael adduct): 3.1% by mass, furfural: 0.03% by mass, benzaldehyde: 0.03% by mass, protoanemonin: 0.02% by mass and water: 8.9% by mass.

The above-mentioned crude acrylic acid-containing solution (the mother liquid) was fed to the distillation column 1 and the distillation column 1 was operated under condition shown in Table 1 to obtain the high boiling point component-containing solution containing the Michael adducts from the bottom of the distillation column 1. The high boiling point component-containing solution obtained at this time contained maleic acid by 62% based on the total amount of maleic acid and maleic anhydride. The amount of Michael adducts were 42% by mass.

The obtained high boiling point component-containing solution was fed to the reaction-distillation apparatus 2 and the reaction apparatus was operated under the same condition as Experimental Example 1-1 to carry out the decomposition of the Michael adducts and collection of the decomposition product. The result is shown in Table 1.

The decomposition operation of the Michael adducts was continued for two weeks, but troubles such as stain in the reaction apparatus and other ancillary facilities such as heat exchanger and pressure rise in the apparatus were not occurred, the viscosity of waste oil was also low and the operation was stably carried out.

The conversion of the Michael adducts at this time was 82% and the yield of acrylic acid for the Michael adducts fed was 80%.

Experimental Example 1-3

Acrylic acid was collected in like manner as Experimental Example 1-2 except that the operation condition of the distillation column 1 (the high boiling point separation column) was changed to the condition shown in Table 1. The high boiling point component-containing solution fed to the reaction distillation apparatus 2 at this time contained maleic acid by 80% based on the total amount of maleic acid and maleic anhydride.

When the decomposition operation of the Michael adducts was carried out, the adherence of stain was confirmed on the heat exchanger E-3. Since the viscosity of waste oil was raised and the pressure of column inside of the reaction distillation apparatus 2 was raised, operation was continued for one week and then stopped. The conversion of the Michael adducts at this time was 72% and the yield of acrylic acid for the Michael adducts fed was 58%. The result is shown in Table 1.

Further, the high boiling point component-containing solution used in Experimental ample 1-3 is residual mother liquid separated from the product after crystallization purification performed in like manner as Experimental Example 1-2. Accordingly, the water content of the residual mother liquid is slightly much in comparison with the crude acrylic acid-containing solution of Experimental Example 1-1 that was obtained through the azeotropic separation step, and it is considered that it was an environment in which maleic anhydride was easily converted to water-including maleic acid at the column bottom (in the column bottom solution) of the distillation column 1 under the condition (the column bottom temperature is slightly low in comparison with Experimental Examples 1-1 and 1-2 and F/B is small) of the high boiling point component separation step adopted in Experimental Example 1-3. It is considered according to the above-mentioned reason that the proportion of the amount of maleic acid of Experimental Example 1-3 was slightly large in comparison with Experimental Examples 1-1 and 1-2.

According to the result of Experimental Examples 1-1 to 1-3, it is understood that when the amount of maleic acid contained in the high boiling point component containing solution fed to the decomposition step is preliminarily reduced, the rise of solution viscosity and the generation of polymers are suppressed and the decomposition of the Michael adducts and collection of decomposition product (acrylic acid) are efficiently.

Experimental Example 2-1

High boiling point component containing solution was obtained in like manner as Experimental Example 1-1 except that the operation condition of the distillation column 1 (the high boiling point separation column) was changed to the condition shown in Table 1. The high boiling point component-containing solution obtained contained maleic acid by 62% based on the total amount of maleic acid and maleic anhydride. Further, acrylic acid dimer (the Michael adduct) was contained by 20% by mass in the high boiling point component-containing solution.

The high boiling point component-containing solution obtained was fed to the reaction distillation apparatus 2 (the distillation column) and the decomposition operation of the Michael adducts was continued for two weeks, but the adherence of stain in the reaction apparatus and other ancillary facilities was not observed. Further, troubles such as pressure rise in the apparatus were not occurred, the viscosity of waste oil was also low and the operation was stably carried out. The conversion of the Michael adducts was 70% and the yield of acrylic acid for the Michael adducts fed was 63%. The result is shown in Table 1.

Experimental Example 2-2

High boiling point component containing solution was obtained in like manner as Experimental Example 1-1 except that the operation condition of the distillation column 1 (the high boiling point separation column) was changed to the condition shown in Table 1. The high boiling point component-containing solution obtained contained acrylic acid dimer (the Michael adduct) by 63% by mass and contained maleic acid by 62% by mass based on the total amount of maleic acid and maleic anhydride.

The high boiling point component-containing solution obtained was fed to the reaction-distillation apparatus 2 and the decomposition operation of the Michael adducts was carried out. Further, the high boiling point component-containing solution fed contained the amount of the Michael adducts a little much compare to Experimental Example 2-1. When the separation column and ancillary facilities were confirmed after the lapse of 2 weeks since starting the decomposition operation, a little amount of stain adheres on a heat exchanger, the rise of the viscosity of waste oil was confirmed. Further, the level of the adherence of stain and the rise of the viscosity of waste oil was a level by which decomposition operation could be tentatively carried out. The conversion of the Michael adducts at this time was 82% and the yield of acrylic acid for the Michael adducts fed was 72%. The result is shown in Table 1.

It is understood according to the result of Experimental Examples 2-1 and 2-2 that the rise of solution viscosity and the generation of polymers are suppressed and the decomposition step is further stably carried out by setting the concentration of the Michael adducts as the preferable range (20 to 60% by mass based on 100% by mass of the high boiling point component-containing solution) of the present invention, in addition to the amount of maleic acid of the high boiling point component-containing solution fed to the decomposition step.

Experimental Example 3-1

The high boiling point component separation step and the decomposition step were carried out in like manner as Experimental Example 1-1 except that the temperature of the position ($16^{th}$ stage among 20 theoretical stages and hereinafter, called as "lower stage") of 80% of the total number of theoretical stage in which the column top side of the reaction-distillation column with tray used as the reaction apparatus is a base point was set as 140° C., and the collection of acrylic acid was carried out. Further, the high boiling point component-containing solution fed to the reaction apparatus contained the Michael adducts by 42% by mass and further, maleic acid by 78% based on the total amount of maleic acid and maleic anhydride. Operation condition and the like are shown in Table 1.

When the distillate from the column top of the reaction-distillation apparatus 2 and accumulated solution at the lower stage of the reaction apparatus were analyzed during operation of the reaction-distillation apparatus 2, maleic acid and maleic anhydride were contained by 8% by mass in total in the distillate and maleic acid and maleic anhydride were contained by 70% by mass in the accumulated solution at the lower stage of the reaction-distillation column.

Although the operation of the reaction distillation apparatus 2 was continued, pressure in the apparatus was raised; therefore the operation was continued for one week and then stopped. The conversion of the Michael adducts was 85% and the yield of acrylic acid for the Michael adducts fed was 78%. The result is shown in Table 1.

In Experimental Example 3-1, temperature nearby the lower stage (16$^{th}$ stage among 20 theoretical stages and a position at 80% of the total number of theoretical stage) of the reaction-distillation column in the decomposition step was set at 140° C. that is slightly higher in comparison with Experimental Example 1-1 (120° C.). As a result, maleic acid is condensed nearby the lower stage in the reaction-distillation column and it is considered that the precipitation of water-including maleic acid and the copolymer with acrylic acid are easily occurred. Further, since the amount of maleic acid contained in the high boiling point component-containing solution was much, it is considered that the amount of maleic acid distilled from the column top side of the reaction-distillation column was increased by heating. Namely, it is considered in Experimental Example 3-1 that although the acrylic acid containing solution in like manner as Experimental Example 1-1 was used, the amount of maleic acid in the high boiling point component-containing solution fed to the decomposition step was heightened because the amount of maleic acid contained in collected acrylic acid (the distillate of the decomposition step) was much.

Experimental Example 3-2

Acrylic acid was collected according to operation and steps in like manner as Experimental Example 1-1. However, the reaction-distillation apparatus (the reaction-distillation column with tray) was operated by setting the temperature of the lower stage (16$^{th}$ stage among 20 theoretical stages) as 110° C. and setting a reflux ratio in the reaction-distillation apparatus as 3. At this time, maleic acid and maleic anhydride were contained by 2% by sass in total in the distillate of the reaction-distillation apparatus and maleic acid and maleic anhydride were contained by 35% by mass in the accumulated solution at the lower stage of the reaction distillation column. The operation condition and the like of the reaction apparatus are shown in Table 1.

The operation of the reaction-distillation column was continued for two weeks, but the adherence of stain in the reaction-distillation apparatus 2 and other ancillary facilities was not observed. Further, troubles such as pressure rise in the apparatus was not occurred, the viscosity of waste oil in the reaction-distillation apparatus 2 (the reaction-distillation column) was also low and the operation was stably carried out. The conversion of the Michael adducts was 86% and the yield of acrylic acid for the Michael adducts fed was 84%. The result is shown in Table 1.

In Experimental Example 3-2, temperature nearby the lower stage of the reaction-distillation column was set at temperature (110° C.) that is slightly lower in comparison with Experimental Example 3-1 to be operated and a reflux ratio was raised; therefore it is considered that problems such as the precipitation of water-including maleic acid, the preparation of polymer and the distillation of maleic acid were suppressed.

Experimental Example 3-3

Acrylic acid was collected according to operation and steps in like manner as Experimental Example 1-1. However, the reaction apparatus (the reaction-distillation column with tray) was operated by setting the temperature of the lower stage (16$^{th}$ stage among 20 theoretical stages) at 120° C. and setting a reflux ratio in the reaction-distillation apparatus as 0.3. Further, the high boiling point component-containing solution fed to the reaction apparatus contained the Michael adducts by 42% by mass and further, maleic acid by 72% based on the total amount of maleic acid and maleic anhydride. Further, maleic acid and maleic anhydride were contained by 6% by mass in total in the distillate of the reaction-distillation column and maleic acid and maleic anhydride were contained by 65% by mass in the accumulated solution at the lower stage of the reaction-distillation column. The operation condition and the like of the reaction apparatus are shown in Table 1.

The operation of the reaction-distillation apparatus 2 was continued for two weeks, but since pressure in the reaction-distillation apparatus 2 was raised, the operation was stopped after one week from the start of operation. The conversion of the Michael adducts was 75% and the yield of acrylic acid for the Michael adducts fed was 62%. The result is shown in Table 1.

According to the results of Experimental Examples 1-1 and 3-1 to 3-3, it is understood that the amounts of maleic acid and maleic anhydride contained in the distillate of the reaction-distillation column is effectively reduced by controlling the temperature of the lower stage of the reaction-distillation column of the decomposition step and adjusting a reflux ratio. Further, it is understood that since this also contributes to reduce the amount of maleic add in the high boiling point component-containing solution fed to the decomposition step to a specific amount or less, acrylic acid is more efficiently collected by employing the above-mentioned condition in the decomposition step.

Experimental Example 4-1

Acrylic acid was collected in like manner as Experimental Example 1-1 except that the operation pressure of the reaction-distillation column was set at 46 hPa (35 torr), decomposition temperature (column bottom temperature) was set at 140° C. and a reflux ratio was set as 1.2. The operation conditions of the distillation column 1 and the reaction-distillation apparatus 2 (the reaction distillation column) are shown in Table 2.

Further, the high boiling point component-containing solution fed to the reaction-distillation apparatus 2 contained maleic acid by 74% based on the total amount of maleic acid and maleic anhydride (the amount of the Michael adduct was 42% by mass). Further, when the composition of the distillate was analyzed during operation of the reaction-distillation apparatus 2, the distillate contained maleic acid and maleic anhydride by 10% by mass.

The operation of the reaction-distillation apparatus 2 was continued, but since the proportion of the amount of maleic acid is high in the high boiling point component-containing solution, the precipitation trouble of maleic acid in the column was occurred and pressure rise in the apparatus was occurred, the operation was stopped after one week from the start of operation of the reaction-distillation apparatus 2. Stain was gradually confirmed in the inside of the column and ancillary facilities such as a heat exchanger. The conversion of the Michael adducts was 68% and the yield of acrylic acid for the Michael adducts fed was 64%. The result is shown in Table 2.

Experimental Example 4-2

Acrylic acid was collected in like manner as Experimental Example 4-1 except that the operation pressure of the reaction-distillation column was set at 467 hPa (350 torr), decomposition temperature (column bottom temperature) was set at 210° C. and a reflux ratio was set as 1.2. The operation conditions of the distillation column 1 and the reaction-distillation apparatus 2 (the reaction distillation column) are shown in Table 2.

Further, the high boiling point component-containing solution fed to the reaction-distillation apparatus 2 contained maleic acid by 50% based on the total amount of maleic acid and maleic anhydride (the amount of the Michael adducts was 42% by mass). Further, when the composition of the distillate was analyzed during operation of the reaction-distillation apparatus 2, the distillate contained maleic acid and maleic anhydride by 8% by mass in total.

The decomposition operation of the Michael adducts was continued for two weeks, but remarkable stain was not confirmed in the reaction-distillation apparatus and other ancillary facilities. Further, pressure rise in the column was not occurred, the viscosity of waste oil was also low and the operation was stably carried out. The conversion of the Michael adducts was 80% and the yield of acrylic acid for the Michael adducts fed was 61%. The result is shown in Table 2.

According to the results of Experimental Examples 1-1, 4-1 and 4-2, it is understood that the amount of maleic acid in the high boiling point component-containing solution fed to the decomposition step is reduced to a specific amount or less, the amounts of maleic acid and maleic anhydride contained in the distillate of the reaction-distillation column is effectively reduced by changing the operation pressure and reaction temperature of the reaction-distillation column to a suitable condition, and acrylic acid is more efficiently collected while preventing the precipitation of maleic acid in the column.

Experimental Example 5

The high boiling point component separation step and the decomposition step were carried out in like manner as Experimental Example 1-1 except that a simple distillation apparatus (an apparatus combining a still and a condenser) were used in place of the reaction-distillation apparatus 2 of the decomposition step. The composition of feed solution to respective steps and operation condition are shown in Table 2.

When the composition of the distillate from the simple distillation apparatus was analyzed, the distillate contained maleic acid and maleic anhydride by 18% by mass in total.

When the decomposition operation of the Michael adducts was continued for one week, stain was confirmed on the distillation apparatus and ancillary facilities such as a heat exchanger. Additionally, solution viscosity in the reaction apparatus was very high. Further, the conversion of the Michael adducts was 83% and the yield of acrylic acid for the Michael adducts fed was 71%. The result is shown in Table 2.

Experimental Example 6

Figure 3:
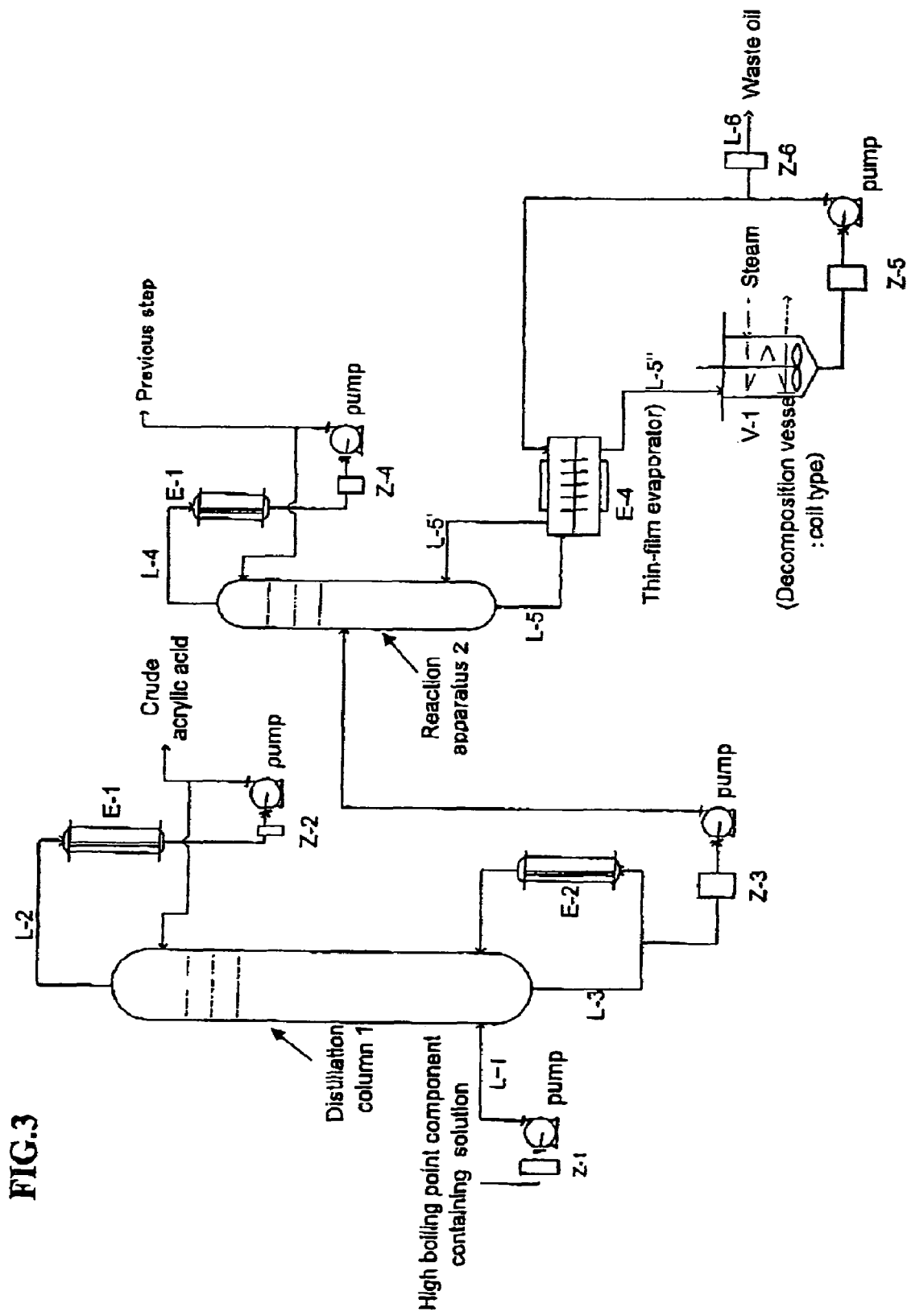
FIG. 3 is a step diagram showing other example of the step of the process for producing acrylic acid related to the present invention.

Acrylic acid was collected according to the steps shown in FIG. 3. Further, in Experimental Example 6, a sieve tray distillation column with the number of stage of 50 stages was used as the distillation column 1 (the high boiling point separation column), the reaction-distillation column with tray (the number of stage: 20 stages, the sieve tray distillation column) was used as the reaction-distillation apparatus 2 of the decomposition step, and a thin-film evaporator as a heat exchanger E-4 equipped with a decomposition vessel V-1 was used as the heat source of the reaction-distillation apparatus 2.

Acrylic acid-containing solution was obtained by the similar method as Experimental Example 1-1 and the acrylic acid-containing solution was introduced into the distillation column 1. The distillation column 1 was controlled at operation pressure: 46.7 hPa (35 mmhg) and column bottom temperature: 98° C., and operated at a reflux ratio: 0.9 and the residence time of the column bottom solution: 5 hours, to obtain the high boiling point component-containing solution containing the Michael adducts from the column bottom of the distillation column 1. Further, crude acrylic acid was obtained from the column top of the distillation column.

Then, the high boiling point component-containing solution obtained was introduced into the reaction-distillation apparatus 2 (the reaction-distillation column with tray, the decomposition step) at 10 kg/hr, acrylic acid and other low boiling point components were evaporated by the thin-film evaporator E-4 to be circulated to the reaction-distillation apparatus 2 and on the other hand, the column bottom solution of the thin-film evaporator E-4 was introduced into the decomposition vessel V-1. The decomposition vessel V-1 was operated at 150° C. (decomposition temperature) and normal pressure, and setting the residence time as 30 hours. The decomposition solution decomposed by heating in the decomposition vessel V-1 was circulated to the thin-film evaporator E-4 with a pump and the decomposition reaction of the Michael adducts and the collection of acrylic acid generated were carried out.

When the decomposition operation of the Michael adducts was continued for three weeks, solution viscosity was raised in the reaction-distillation apparatus 2 and slight stain was confirmed on the reaction distillation apparatus 2 and the ancillary facilities such as the heat exchanger although continuous operation was in a possible level. The conversion of the Michael adducts was 70% and the yield of acrylic acid for the Michael adducts fed was 60%. Decomposition condition and the result are shown in Table 2.

Experimental Example 7

The collection of acrylic acid was carried out in like manner as Experimental Example 1-1 except that aqueous solution (aqueous solution of 50% by mass) containing 4H-TEMPO (4-hydroxy-2,2,6,6-tetramethylpyperizinoxyl) was introduced at 0.06 kg/hr from the column top side of the distillation column 1.

The decomposition operation of the Michael adducts was continued for two weeks, but stain was not observed in the reaction-distillation apparatus 2 and other ancillary facilities and pressure rise in the column was not occurred. Further, the viscosity of the waste oil was also low and the reaction-distillation column was stably operated. In particular, the adherence of polymers in the system of the decomposition of the Michael adducts was also a little in comparison with other Experimental Examples and the viscosity of the waste oil was also low. The conversion of the Michael adducts was 88% and the yield of acrylic acid for the Michael adducts fed to the decomposition step was 86%. Decomposition condition and the result are shown in Table 2.

Experimental Example 8

The collection of acrylic acid was carried out in like manner as Experimental Example 1-1 except that the decomposition temperature (column bottom temperature) was set at 170° C., the temperature of the heat source of a forced circulation type heat exchanger was set at 220° C. and the reaction-distillation apparatus 2 was operated at the condition of temperature difference (ΔT) between the decomposition temperature and the heat source of the forced circulation type heat exchanger by 100° C.

When the decomposition operation of the Michael adducts was continued for two weeks, stain was observed on the heat transfer surface of the heat exchanger. The conversion of the Michael adducts was 82% and the yield of acrylic acid for the Michael adducts fed was 78%. The result is shown in Table 2.

TABLE 1

| | Experimental Example 1-1 | Experimental Example 1-2 | Experimental Example 1-3 | Experimental Example 2-1 | Experimental Example 2-2 | Experimental Example 3-1 | Experimental Example 3-2 | Experimental Example 3-3 |
|---|---|---|---|---|---|---|---|---|
| High boiling point component separation step | | | | | | | | |
| Column bottom temperature ° C. | 98 | 110 | 84 | 96 | 100 | 86 | 98 | 87 |
| Residence time hr | 5 | 10 | 5 | 5 | 5 | 6 | 6 | 5 |
| F/B*[1] fold | 12 | 12 | 4 | 9 | 18 | 4 | 12 | 4 |
| Composition of high boiling point component-containing solution (feed solution for decomposition step) | | | | | | | | |
| Proportion of the amount of water-including maleic acid*[2] % | 38 | 62 | 80 | 62 | 62 | 78 | 38 | 72 |
| Total amount of maleic acid % by mass*[3] | 9.8 | 9.8 | 9.8 | 9.8 | 9.8 | 15 | 9.8 | 9.8 |
| Michael adducts % by mass | 42 | 42 | 42 | 20 | 63 | 42 | 42 | 42 |
| Decomposition step | | | | | | | | |
| Decomposition temperature ° C. | 170 | 170 | 170 | 170 | 170 | 170 | 170 | 170 |
| Residence time*[4] hr | 6 | 6 | 6 | 6 | 6 | 6 | 6 | 6 |
| Lower stage temperature*[5] ° C. | 110 | 110 | 110 | 110 | 110 | 140 | 110 | 120 |
| Maleic acid concentration at lower stage (in total)*[6] % by mass | 45 | 45 | 45 | 45 | 45 | 70 | 35 | 65 |
| Distilled maleic acid concentration (in total) % by mass | 2 | 2 | 2 | 2 | 2 | 8 | 2 | 6 |
| Operation pressure hPa | 267 | 267 | 267 | 267 | 267 | 267 | 267 | 267 |
| Reflux ratio | 1.2 | 1.2 | 1.2 | 1.2 | 1.2 | 1.2 | 3 | 0.3 |
| Catalyst | | | | | | | | |
| N-oxyl (4H-TEMPO) | Not used | Not used | Not used | Not used | Not used | Not used | Not used | Not used |
| Decomposition efficiency of Michael adducts | | | | | | | | |
| Conversion % | 85 | 82 | 72 | 70 | 82 | 85 | 86 | 75 |
| Selectivity % | 98 | 98 | 80 | 90 | 72 | 92 | 98 | 83 |
| Yield % | 83.3 | 80.4 | 57.6 | 63.0 | 59.0 | 78.2 | 84.3 | 62.0 |
| Waste oil viscosity mPas/100° C. | 35 | 70 | 300 | 40 | 152 | 250 | 30 | 230 |

TABLE 2

| | Experimental Example 4-1 | Experimental Example 4-2 | Experimental Example 5 | Experimental Example 6 | Experimental Example 7 | Experimental Example 8 |
|---|---|---|---|---|---|---|
| High boiling point component separation step | | | | | | |
| Column bottom temperature ° C. | 98 | 98 | 98 | 98 | 98 | 98 |
| Residence time hr | 5 | 5 | 5 | 5 | 5 | 5 |
| F/B*[1] fold | 12 | 12 | 12 | 12 | 12 | 12 |
| Composition of high boiling point component-containing solution (feed solution for decomposition step) | | | | | | |
| Proportion of the amount of water-including maleic acid*[2] % | 74 | 60 | 72 | 38 | 38 | 38 |

TABLE 2-continued

|  | Experimental Example 4-1 | Experimental Example 4-2 | Experimental Example 5 | Experimental Example 6 | Experimental Example 7 | Experimental Example 8 |
|---|---|---|---|---|---|---|
| Total amount of maleic acid % by mass*3 | 12 | 5 | 15 | 9.8 | 9.8 | 9.8 |
| Michael adducts % by mass | 42 | 42 | 42 | 42 | 42 | 42 |
| Decomposition step |  |  |  |  |  |  |
| Decomposition temperature ° C. | 140 | 210 | 170 | 150 | 160 | 170 |
| Residence time*4 hr | 12 | 6 | 6 | 30 | 6 | 6 |
| Lower stage temperature*6 ° C. | 100 | 150 | None | 110 | 110 | 110 |
| Maleic acid concentration at lower stage (in total)*5 % by mass | 20 | 70 | None | 45 | 46 | 46 |
| Distilled maleic acid concentration (in total) % by mass | 10 | 8 | 18 | 1 | 2 | 2 |
| Operation pressure hPa | 46 | 467 | 267 | 47 | 267 | 267 |
| Reflux ratio | 1.2 | 1.2 | None | 1.2 | 1.2 | 1.2 |
| Catalyst |  |  |  |  |  |  |
| N-oxyl (4H-TEMPO) | Not used | Not used | Not used | Not used | Used | Not used |
| Decomposition efficiency |  |  |  |  |  |  |
| of Michael adducts |  |  |  |  |  |  |
| Conversion % | 68 | 80 | 83 | 70 | 88 | 82 |
| Selectivity % | 94 | 70 | 85 | 85 | 98 | 95 |
| Yield % | 63.9 | 60.8 | 70.6 | 59.5 | 86.2 | 78.0 |
| Waste oil viscosity mPas/100° C. | 32 | 102 | 203 | 150 | 28 | 120 |

Further, "F/B (*1)" in Tables 1 and 2 means the feed rate (kg/hr)/the feed rate (kg/hr) of extract solution (column bottom solution) of feed solution to the high boiling point component separation step, the "Proportion of the amount of water-including maleic acid (*2)" means the proportion of the amount of water-including maleic acid calculated from the above-mentioned equation (1), the "Total amount of maleic acid (*3)" means the total amount of maleic acid and maleic anhydride, the "Residence time (*4)" means a value calculated by the equation of "the retained solution mass (kg) in the reaction apparatus/the feed rate (kg/hr) of extract solution discharged from reaction apparatus", and the "Lower stage (*5)" means $16^{th}$ stage of the reaction distillation column with stage having 20 theoretical stages (a position of 80% of the total theoretical stage in which the column top side is a base point) respectively.

[Preparation of Catalyst]

Catalyst I

Molybdenum-bismuth catalyst was prepared according to the description of Example 1 of JP-A-2000-325795. This is referred to as the catalyst (I). The metal element composition (atomic ratio excluding oxygen and hereinafter, the same) of the catalyst (I) was $Mo_{12}W_{0.2}Bi_{1.7}Fe_{1.5}Co_4Ni_3K_{0.08}Si$.

Catalyst II

Molybdenum-vanadium catalyst was prepared according to the description of Example 1 of JP-A-8-206504. This is referred to as the catalyst (II). The metal element composition (atomic ratio excluding oxygen) of the catalyst (II) was $Mo_{12}V_{6.1}W_1Cu_{2.3}Sb_{1.2}$.

Experimental Example 9

Figure 5:
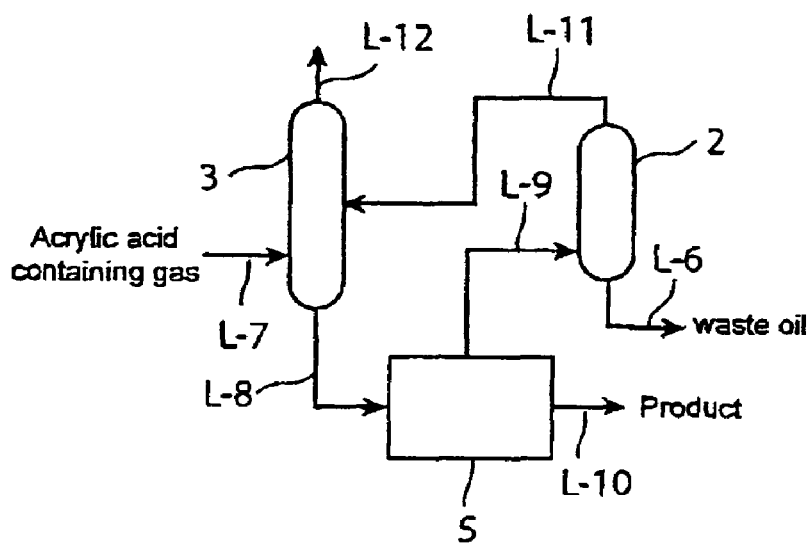
FIG. 5 is a step diagram showing other example of the step of the process for producing acrylic acid related to the present invention.

Acrylic acid was produced according to steps shown in FIG. 5.

[Synthesis of Acrylic Acid]

For the synthesis of acrylic acid was used a reactor that was equipped with a jacket for circulation of a heating medium at an outer periphery, stored a reaction tube with an inner diameter of 25 mm and a length of 7000 mm in the inside and was equipped with a porous pipe plate with a thickness of 75 mm that divides the heating medium jacket into 2 to up and down at a position of 3500 mm from the lower portion of the jacket.

The heating medium was respectively circulated to the lower portion (the first reaction zone) and the upper portion (the second reaction zone) of the reactor to control temperature, and (1) ceramic balls (a layer length of 250 mm) with an average diameter of 5 mm, (2) a mixture in which the catalyst (I) was mixed with the ceramic balls with au average diameter of 5 mm at a proportion of 70:30 (a layer length of 700 mm), (3) the catalyst (I) (a layer length of 2,300 mm), (4) Raschig rings (a layer length of 500 nm) made of stainless with an outer diameter of 5 mm, an inner diameter of 4.5 mm and a length of 6 mm, (5) a mixture in which the catalyst (II) was mixed with the ceramic balls with an average diameter of 5 mm at a proportion of 75:25, (a layer length of 600 mm) and (6) the catalyst (II) (a layer length of 1900 mm) were packed in this order from the lower portion to the upper portion of the reaction tubes.

Propylene, air (a moisture concentration of 2% by mass) and the portion of discharge gas from the absorption column 3 (recycle gas) were circulated and respective feed rates and the cooling temperature of recycle gas were adjusted to be fed so that the space velocity of the first reaction zone was 1250 hr$^{-1}$ (STP). Further, the composition of mix gas comprising the raw material and recycle gas that was circulated in the first reaction zone was propylene; 8.0% by volume, $O_2$: 14.4% by volume, $H_2O$: 2.0% by volume and $N_2$, propane, COx, acrylic acid, acetic acid and the like as residue.

The temperatures of the heating medium in the first reaction zone and the second reaction zone were respectively adjusted so that propylene conversion at the outlet (outlet pressure (absolute pressure) 0.15 MPa) of the second reaction zone was 97±0.5% by mol and acrolein conversion was 1±0.5% by mol and acrylic acid-containing gas containing 16.62% by mass of acrylic acid was obtained at 18.77 kg/hr.

Then, the acrylic acid-containing gas cooled to 200° C. by a pre-cooler was introduced to the acrylic acid absorption column 3 and absorbed as the acrylic acid solution.

The acrylic acid absorption column 3 is a packed column packing regular filling materials, has the theoretical stage of 21 stages, is equipped with the feed orifice of the acrylic acid-containing gas and the extract outlet of absorption solution at the column bottom portion, the introduction inlet of aqueous solution for absorb and the discharge orifice of gas at the column bottom portion and the feed pipe of the distillate (circulation solution) from the reaction distillation apparatus of the decomposition step at the column side portion ($19^{th}$ of the theoretical stage), and further equipped with a cooler (not illustrated) for cooling the portion of gas discharged from the column top portion.

As the absorption solvent of acrylic acid, water containing hydroquinone equivalent to 200 ppm by mass for the amount of acrylic acid in the acrylic acid-containing gas introduced in the absorption column 3 is used and this was fed to the absorption column 3 at 1.01 kg/hr.

Further, the operation of the absorption column 3 at absorbing the acrylic acid-containing solution was carried out at the column top temperature of 66.9° C., the column top pressure of 0.11 MPa, the cooling temperature of recycle gas of 40.6° C. and a recycle rate of 29.0%. At this time, all of the condensate obtained by cooling the recycle gas was circulated to the absorption column 3.

The distillate (circulation solution) from the reaction-distillation apparatus 2 of the decomposition step was fed at 2.33 kg/hr from the column side portion of the absorption column 3.

The absorption efficiency of acrylic acid in the absorption column 3 was 98.22%.

[Crystallization Purification Step]

Then, the acrylic acid-containing aqueous solution obtained in the absorption column 3 was fed to the dynamic crystallization apparatus (purification apparatus) 5 and purification was carried out by dynamic crystallization by 4 times.

The dynamic crystallization was carried out by a crystallization purification apparatus in accordance with the crystallization apparatus described in JP-B-S53-41637. The apparatus is a metal pipe with a length of 6 m and an inner diameter of 70 mm equipped with a storage apparatus at a lower portion, liquid is transferred to the upper position of the pipe by a circulation pump and the liquid is designed to be able to be flown in failing film state. The outer surface of the pipe is composed of a double jacket and the jacket is designed to be constant temperature by a thermostat. Further, dynamic crystallization once was carried out by the procedure below.

1. Crystallization:

The acrylic acid-containing solution fed to a storage vessel was flown on pipe wall in falling film state by a circulation pump, the temperature of a jacket was lowered to a coagulation point or less and about 60 to 80% by mass of acrylic acid containing in the acrylic acid-containing solution fed to the storage vessel was crystallized on the wall surface.

2. Sweating:

The circulation pump was let stopped, the temperature of the jacket was raised to nearby the coagulation point and about 2 to 5% by mass of acrylic acid crystallized was let to cause sweating. After the sweating, the residual acrylic acid-containing solution in the storage vessel and sweating solution were pumped out.

3. Melting:

The temperature of the jacket was raised to the coagulation point or more to melt crystals and the melt was pumped out.

In the above operations, the temperature and coagulation point were respectively dependent on respective steps. Thereby, acrylic acid having purity of 99.89% by mass was obtained at 3.12 kg/hr.

Further, the composition of the residual mother liquid taken out from the dynamic crystallization apparatus was water: 9% by mass, acetic acid: 3.7% by mass, maleic acid: 0.9% by mass, furfural: 1.1% by mass, benzaldehyde: 0.3% by mass and acrylic acid dimer (the Michael adducts): 3.4% by mass.

[Decomposition Step]

The residual mother liquid containing the Michael adducts taken out from the dynamic crystallization apparatus 5 at crystallization purification step was fed to the reaction-distillation apparatus 2 and the Michael adducts were decomposed to be collected as acrylic acid As the reaction distillation apparatus 2, a distillation column equipped with a forced circulation type external heat exchanger was adopted and the thermal decomposition of the Michael adducts was carried out at conditions of thermal decomposition temperature (column bottom temperature): 170° C., residence time: 4 hours, column top pressure: 26.6 kPa and column top temperature: 98° C. Further, steam of 2.5 MPaG was used as the heat source of the forced circulation type external heat exchanger, shell pressure was 1.3 MPaG (heating temperature: 195° C.) and the circulation amount of the column bottom solution was equivalent to 200 $m^3$/hr (further, the value of the circulation amount indicates a converted value converted to a value of a case being carried out in a plant, based on the value of Example 1 carried out in a miniature plant). The temperature difference ($\Delta T$) between decomposition temperature and the heat source of the forced circulation type external heat exchanger was 25° C.

The conversion of the Michael adducts was 70% and the selectivity of acrylic acid was 75%. Further, the viscosity of waste oil (a vibration viscometer and solution temperature: 100° C.) was 150 mPas.

Acrylic acid was collected at 2.33 kg/hr from the column top position of the reaction-distillation apparatus 2 and circulated to the column side position of the absorption column 3 through the line 9. The composition of the distillate (circulation solution) distilled from the reaction-distillation apparatus 2 is shown in Table 3 described later.

When crystals taken out from the dynamic crystallization apparatus were finally analyzed, the purity of acrylic acid was 99.89% by mass and it contained water: 550 ppm (based on mass, and hereinafter, same), acetic acid: 520 ppm, maleic acid: 15 ppm, furfural: 0.8 ppm, benzaldehyde: 0.5 ppm, formaldehyde: 0% by mass and acrylic acid dimer: 50 ppm by mass.

After operation for 14 days, adhered matters were partially confirmed in the reaction-distillation apparatus. The mass of the adhered matters in the reaction apparatus was 200 g converted to per one day.

The measurement result of the above-mentioned conversion of the Michael adducts, the selectivity of acrylic acid and the viscosity of waste oil and the like is shown in Table 4.

Experimental Example 10

In Experimental Example 10, acrylic acid was produced by carrying out operation in like manner as Experimental Example 9, except that a distillation column with tray was employed as the reaction-distillation apparatus 2 at the decomposition step. The reaction-distillation apparatus with tray used was equipped with sieve trays of 20 stages (equivalent to the 5 stages of the theoretical stage) and a forced circulation type external heat exchanger (not illustrated). The decomposition step of the Michael adducts is illustrated below.

[Decomposition Step]

The residual mother liquid obtained in the crystallization apparatus 5 was fed to the lower stage of the reaction-distillation apparatus 2 with tray (distillation column with tray). The thermal decomposition of the Michael adducts was carried out at conditions of thermal decomposition temperature (column bottom temperature): 170° C., residence time: 4 hours, column top pressure: 26.6 kPa, a reflux ratio: 1.5 and column top temperature: 98° C. The operation of the forced circulation type external heat exchanger was adjusted so as to be circulation amount similar as Example 9. The temperature difference (ΔT) between decomposition temperature and the heat source of the forced circulation type external heat exchanger was 25° C. The conversion of the Michael adducts was 72% and the selectivity of acrylic acid was 80%. Further, the viscosity of waste oil was 118 mPas and troubles such as stain in the reaction-distillation apparatus 2 were not confirmed in operation for 14 days (the amount of adhered matters in the reaction apparatus after operation for 14 days: 120 g/day).

Acrylic acid was collected at 2.33 kg/hr from the column top position of the reaction-distillation apparatus 2 and circulated to the column side position of the absorption column 3. The composition of the distillate is shown in Table 3 and the measurement result of the conversion of the Michael adducts, the selectivity of acrylic acid and the viscosity of waste oil and the like is shown in Table 4.

Further, crystals taken out from the dynamic crystallization apparatus were the purity of acrylic acid of 99.89% by mass and contained water: 520 ppm by mass, acetic acid: 480 ppm by mass, maleic acid: 12 ppm by mass, furfural: 0.5 ppm by mass, benzaldehyde: 0.4 ppm by mass, formaldehyde: 0 ppm by mass and acrylic acid dimer: 40 ppm by mass.

Experimental Example 11

Acrylic acid was produced according to steps shown in FIG. 1.

Further, in Experimental Example 11, operation in like manner as Experimental Example 9 was carried out except that the high boiling point component separation step was provided before the decomposition step. Operation after the crystallization purification step is illustrated below.

[High Boiling Point Component Separation Step]

The residual mother liquid obtained by the crystallization apparatus 5 was fed to the middle stage (10$^{th}$ stage among 20 stages and hereinafter, called as "middle stage") of the distillation column 1 (the high boiling point component separation column) equipped with sieve trays with the stage number of 20 stages and a reboiler. The distillation column 1 was controlled at the conditions of operation pressure: 9.3 kPa and a reflux ratio: 0.3.

Acrylic acid was collected at 2.33 kg/hr from the column top position of the distillation column 1 and this was circulated to the column side position of the absorption column 3. The composition of the distillate from the distillation column 1 is shown in Table 3.

[Decomposition Step]

The column bottom solution of the distillation column 1 was fed to the reaction-distillation apparatus 2 and the Michael adducts contained in the column bottom solution were decomposed to be collected as acrylic acid. The operation of the forced circulation type heat exchanger was adjusted so as to be circulation amount in like manner as Experimental Example 9. Further, the composition of the column bottom solution of the distillation column 1 was acrylic acid: 22.1% by mass, maleic acid: 15.2% by mass, furfural: 4.3% by mass, benzaldehyde: 3.9% by mass, acrylic acid dimer: 44.9% by mass and other impurities: 9.6% by mass.

Further, the reaction-distillation apparatus 2 employed was equipped with a forced circulation type external heat exchanger and the thermal decomposition of the Michael adducts was carried out at conditions of thermal decomposition temperature (column bottom temperature): 170° C., residence time: 4 hours, column top pressure: 26.6 kPa and column top temperature: 98° C. The temperature difference (ΔT) between decomposition temperature and the heat source of the forced circulation type heat exchanger was 25° C. The conversion of the Michael adducts was 75% and the selectivity of acrylic acid was 90%. Further, the viscosity of waste oil was 100 mPas and troubles such as stain in the reaction-distillation apparatus 2 were not confirmed in operation for 14 days (the amount of adhered matters in the reaction apparatus after operation for 14 days: 100 g/day). The measurement result of the conversion of the Michael adducts, the selectivity of acrylic acid and the viscosity of waste oil and the like is shown in Table 4.

Acrylic acid collected from the reaction-distillation apparatus 2 was fed to the lower stage of the distillation column 1.

When the crystals taken out from the dynamic crystallization apparatus were analyzed, the purity of acrylic acid was 99.91% by mass and contained water: 470 ppm by mass, acetic acid: 420 ppm by mass, maleic acid: 10 ppm by mass, furfural: 0.2 ppm by mass, benzaldehyde: 0.2 ppm by mass, formaldehyde: 0 ppm by mass and acrylic acid dimer: 40 ppm by mass.

Experimental Example 12

In Experimental Example 12, operation in like manner as Experimental Example 11 was carried out except that the distillation column with tray was used as the reaction-distillation apparatus 2. Operation after the crystallization purification step is illustrated below.

[High Boiling Point Component Separation Step]

The residual mother liquid obtained from the crystallization apparatus 5 was fed to the middle stage (10$^{th}$ stage among 20 stages) of the distillation column 1 equipped with sieve trays with the stage number of 20 stages and a reboiler. The distillation column 1 was controlled at the conditions of operation pressure: 93 hPa and a reflux ratio: 0.3.

Acrylic acid was collected at 2.33 kg/hr from the column top position of the distillation column 1 and this was circulated to the column side position of the absorption column 3. The composition of the distillate is shown in Table 3.

[Decomposition Step]

On the other hand, the column bottom solution of the distillation column 1 was fed to the reaction-distillation apparatus 2 (the distillation column with tray) and the Michael adducts contained in the column bottom solution were decomposed to be collected as acrylic acid. The composition of the column bottom solution was acrylic acid: 22.1% by mass, maleic acid: 15.2% by mass, furfural: 4.3% by mass, benzaldehyde: 3.9% by mass, acrylic acid dimer: 44.9% by mass and other impurities: 9.6% by mass. Further, the reaction-distillation apparatus 2 employed was equipped with sieve trays the reaction-distillation apparatus 2 employed was equipped with sieve trays with 20 stages and a forced circulation type external heat exchanger (not illustrated) and the thermal decomposition of the Michael adducts was carried out at conditions of thermal decomposition temperature (column bottom temperature): 170° C., residence time: 4 hours, column top pressure: 26.6 kPa, reflux ratio: 1.5, and column top temperature: 98° C. The operation of the forced circulation type external heat exchanger was adjusted so as to be circulation amount in like manner as Experimental Example 9. The temperature difference (ΔT) between decomposition temperature and the heat source of the forced circulation type heat exchanger was 25° C. The conversion of the Michael adducts was 82% and the selectivity of acrylic acid was 98%. Further, the viscosity of waste oil was 85 mPas and troubles such as stain in the reaction distillation apparatus 2 were not confirmed in operation for 14 days (the amount of adhered matters in the reaction apparatus after operation for 14 days: 20 g/day). The measurement result of the conversion of the Michael adducts, the selectivity of acrylic acid and the viscosity of waste oil and the like is shown in Table 4.

Acrylic acid collected from the reaction-distillation apparatus 2 was fed to the lower stage of the distillation column 1.

When the crystals taken out from the dynamic crystallization apparatus were finally analyzed, the purity of acrylic acid was 99.92% by mass and contained water: 400 ppm by mass, acetic acid: 400 ppm by mass, maleic acid: 4 ppm by mass, furfural: 0.1 ppm by mass, benzaldehyde: 0.1 ppm by mass, formaldehyde: 0 ppm by mass and acrylic acid dimer: 40 ppm by mass.

Experimental Example 13

Figure 6:
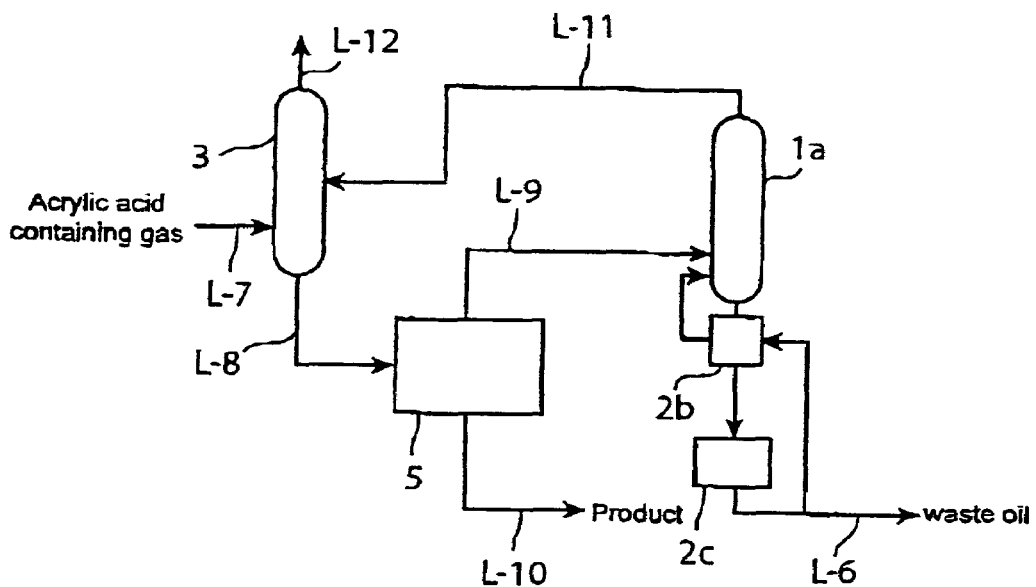
FIG. 6 is a step diagram of the process for producing acrylic acid adopted in Example 13.

Acrylic acid was produced according to steps shown in FIG. 6.

In Experimental Example 13, operation in like manner as Experimental Example 9 was carried out except that the distillation column with tray 1 (equipped with sieve trays with 20 stages) that combined a thin-film evaporator 2b heating residual mother liquid and a decomposition vessel 2c carrying out the decomposition of the Michael adducts was employed in a Michael adduct decomposition step.

[Decomposition Step]

The residual mother liquid containing the Michael adducts that was taken out from the dynamic crystallization apparatus 5 of a crystallization purification step was fed to the lower stage of the distillation column 1 and the decomposition of the Michael adducts was carried out. In the decomposition vessel 2c, the thermal decomposition of the Michael adducts was carried out at conditions of thermal decomposition vessel temperature (decomposition temperature); 170° C. and normal pressure and residence time: 4 hours, the portion of the decomposition solution was fed again to the thin-film evaporator 2b with a pump and residue was discarded. At this time, the thin-film evaporator 2b and the distillation column 1 were controlled so that the column bottom solution was 95° C. and operation was carried out at the conditions of column top pressure: 4.5 kPa, column top temperature: 60° C. and a reflux ratio: 1.5 to collect acrylic acid. At this time, the conversion of the Michael adducts was 72% and the selectivity of acrylic acid was 80%. Further, the viscosity of waste oil was 123 mPas and stain was confirmed in the portion of inside of the distillation column 1 in operation for 14 days (the amount of adhered matters in the distillation column after operation for 14 days: 500 g/day). The measurement result of the conversion of the Michael adducts, the selectivity of acrylic acid and the viscosity of waste oil and the like is shown in Table 4.

Acrylic acid was collected at 2.33 kg/hr from the column top portion of the distillation column 1 and this was circulated to the column side portion of the absorption column 3. The composition of the distillate is shown in Table 3.

When crystals taken out from the dynamic crystallization apparatus were finally analyzed, the purity of acrylic acid was 99.88% by mass and contained water: 600 ppm by mass, acetic acid: 530 ppm by mass, maleic acid: 30 ppm by mass, furfural: 1.8 ppm by mass, benzaldehyde: 1.0 ppm by mass, formaldehyde: 0 ppm by mass and acrylic acid dimer: 60 ppm by mass. The amount of furfural in the product of acrylic acid was high and there was a problem in quality.

Experimental Example 14

Figure 7:
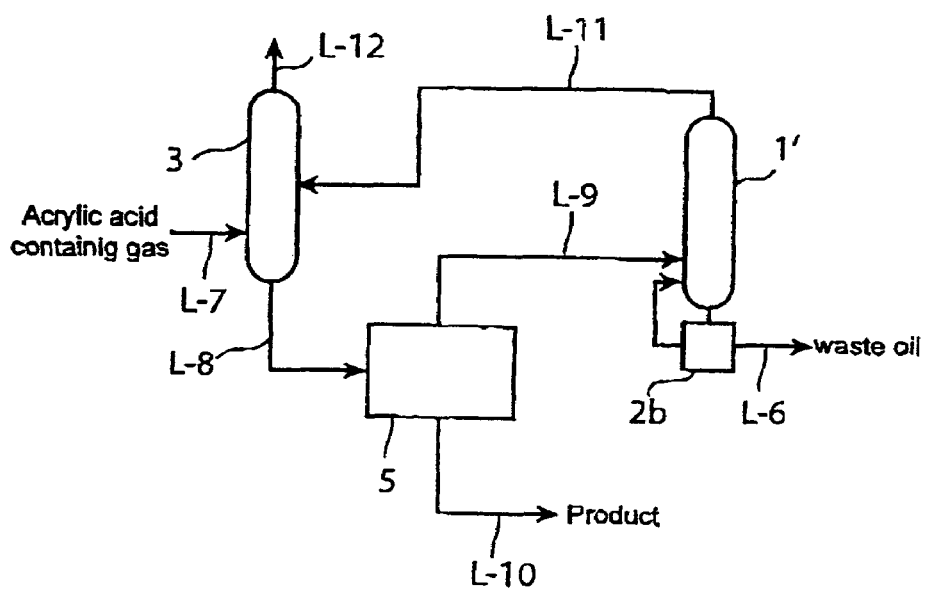
FIG. 7 is a step diagram the process for producing acrylic acid adopted in Example 14.

Acrylic acid was produced according to steps shown in FIG. 7.

In Experimental Example 14, operation in like manner as Experimental Example 9 was carried out except that the distillation column 1 and a thin-film evaporator 2b heating residual mother liquid and decomposing Michael adducts were used in place of the reaction-distillation apparatus, in the decomposition step of the Michael adducts. Further, the thin-film evaporator 2b and the distillation column 1 were controlled so that the column bottom solution was 95° C. and operation was carried out at the conditions of column top pressure: 26.6 kPa, column top temperature: 98° C. and a reflux ratio: 1.5 to collect acrylic acid. At this time, the viscosity of waste oil was 160 mPas and stain was confirmed in the portion of the distillation column 1 in operation for 14 days (the amount of adhered matters in the distillation column after operation for 14 days: 450 g/day)

Acrylic acid was collected at 2.33 kg/hr from the column top portion of the distillation column 1 and this was circulated to the column side portion of the absorption column 3. The composition of the distillate is shown in Table 3 and the measurement result of the conversion of the Michael adducts, the selectivity of acrylic acid and the viscosity of waste oil and the like is shown in Table 4.

When crystals taken out from the dynamic crystallization apparatus were finally analyzed, the purity of acrylic acid was 99.89% by mass and contained water: 550 ppm by mass, acetic acid: 23 ppm by mass, maleic acid: 1.5 ppm by mass, furfural: 0.8 ppm by mass, benzaldehyde: 0 ppm by mass, formaldehyde: 50 ppm by mass and acrylic acid dimer: 0.2 ppm by mass.

By Table 3 collecting the composition of the distillates in respective Experimental Examples, it is understood that the amounts of maleic acid in the distillates are reduced to a low level and the decomposition of the Michael adducts and the collection of acrylic acid are efficiently carried out in Experimental Examples 11 and 12 that carried out the decomposition of the Michael adducts by the reaction-distillation process through the high boiling point component separation step. Further, it is understood that the decomposition effi-

TABLE 3

| (Unit % by mass) | Experimental Example 9 | Experimental Example 10 | Experimental Example 11 | Experimental Example 12 | Experimental Example 13 | Experimental Example 14 |
|---|---|---|---|---|---|---|
| Composition of distillate in decomposition step | | | | | | |
| Acrylic acid | 82.9 | 83.8 | 84.2 | 84.7 | 80.7 | 82.3 |
| Water | 9.1 | 9.1 | 9.2 | 9.2 | 9.1 | 9.0 |
| Acetic acid | 3.7 | 3.7 | 3.8 | 3.8 | 3.7 | 3.6 |
| Maleic acid | 1.0 | 0.5 | 0.1 | 0.07 | 2.2 | 2.2 |
| Furfural | 1.6 | 1.3 | 1.2 | 0.9 | 2.2 | 1.2 |
| Benzaldehyde | 0.5 | 0.4 | 0.4 | 0.33 | 0.7 | 0.4 |
| Formaldehyde | 0.1 | 0.1 | 0.1 | 0.1 | 0.1 | 0.1 |
| Dimer etc. | 0.2 | 0.2 | 0.2 | 0.1 | 0.5 | 0.4 |
| Others | 0.9 | 0.9 | 0.8 | 0.8 | 0.8 | 0.8 |

TABLE 4

| | Experimental Example 9 | Experimental Example 10 | Experimental Example 11 | Experimental Example 12 | Experimental Example 13 | Experimental Example 14 |
|---|---|---|---|---|---|---|
| Composition of high boiling point component-containing solution (feed solution of decomposition step) | | | | | | |
| Proportion of the amount of water including maleic acid [%] | 74 | 72 | 50 | 32 | 75 | 77 |
| Total amount of maleic acid [% by mass] | 12 | 12 | 10 | 10 | 14 | 15 |
| Decomposition efficiency of Michael adducts | | | | | | |
| Conversion [%] | 70 | 72 | 75 | 82 | 65 | 60 |
| Selectivity [%] | 75 | 80 | 90 | 98 | 75 | 70 |
| Yield [%]* | 52.5 | 57.6 | 67.5 | 80.4 | 48.8 | 42 |
| Viscosity [mPas] | 150 | 118 | 100 | 85 | 123 | 160 |
| Stain [g/day] | 200 | 120 | 100 | 20 | 500 | 450 |

Further, in Table 4, water-including maleic acid and the total amount of maleic acid represent respective proportions and amounts contained in the high boiling point component containing solution. Specifically, the "proportion of the amount of water-including maleic acid" indicates the proportion of weight of maleic acid calculated by the above-mentioned equation (1), the "total amount of maleic acid" indicates the total amount of the water-including maleic acid and maleic anhydride, and the "yield [%]" indicates the decomposition efficiency of Michael adducts, which indicates a value calculated by the under-mentioned equation (4).

[Equation 4]

$$\text{Yield [\%]} = \frac{\text{Conversion} \times \text{Selectivity}}{100} \quad (4)$$

ciency of the Michael adducts is high and the amount of adhered matters in the reaction-distillation column carrying out the decomposition of the Michael adducts is also little in comparison with a case of carrying out the decomposition of the Michael adducts by a conventional process (Experimental Examples 13 and 14) (Table 4). Further, since Experimental Examples 9 and 10 employ the reaction-distillation process for the decomposition step of the Michael adducts, the Michael adducts are efficiently decomposed to a certain degree and the collection of acrylic acid is carried out, but since the high boiling point component separation step is not provided, the amount of adhered matters in the reaction-distillation column and viscosity become high compare to reaction of Experimental Examples 11 and 12. Further, in case of employing the crystallization purification step for the purification step, when the amount of maleic acid in the residual mother liquid is inadequate, the residual mother liquid may be directly fed to the decomposition step without passing through the high boiling point component separation step. However, it is preferable to provide the high boiling point component separation step from the viewpoint of industrial efficiency.

The either of the above-mentioned Experimental Examples 13 and 14 is examples that do not carry out the decomposition by the reaction-distillation process. Yield is low and the decomposition efficiency of the Michael adducts is inferior in comparison with other examples Experimental Example 13 uses a decomposition vessel at the decomposition step and it is considered that acrylic acid prepared by the decomposition remains in the decomposition vessel and the decomposition reaction by the reaction-distillation process did not occur. On the other hand, Experimental Example 14 is an example that did not use the reaction-distillation apparatus. Further, although the thin-film evaporator is used as heat source, the heating of the residual mother liquid is inadequate and it is considered that only distillation occurred in the distillation column. Further, since residence time enough for carrying out the decomposition reaction by the reaction-distillation process cannot be secured, it is difficult to carry out the substantial decomposition reaction of the Michael adducts.

Namely, when the reaction-distillation process is adopted for the decomposition step, the precipitation of maleic acid is suppressed at the decomposition step and the residual mother liquid is treated at high temperature and low residence time; therefore it is grasped that the preparation amount of adhered matters in the reaction-distillation column is little and acrylic acid is efficiently produced. Further, it is grasped that the decomposition of the Michael adducts and the collection of acrylic acid are further efficiently carried out by providing the high boiling point component separation step.

INDUSTRIAL AVAILABILITY

According to the process for producing acrylic acid of the present invention, since troubles such as the precipitation of maleic acid and pressure rise in the decomposition apparatus derived from this occur hardly in the decomposition step of the Michael adducts, the decomposition of the Michael adducts is efficiently promoted and acrylic acid is efficiently and stably produced.

This application is based on Japanese Patent application serial no. 2005-352719 filed in Japan Patent Office on Dec. 6, in 2006 and no. 2006-189542 filed in Japan Patent Office on Jul. 10, in 2006, the contents of which are hereby incorporated by reference.

Although the present invention has been fully described by way of examples, it is to be understood that various changes and modifications will be apparent to those skilled in the art, therefore, unless otherwise such changes and modifications depart from the scope of the present invention hereinafter defined, they should be construed as being included therein.

What is claimed is:

1. A method for producing acrylic acid, comprising
   (a) an absorption step of absorbing an acrylic acid-containing gas obtained by oxidizing a raw material gas in gas phase as a crude acrylic acid-containing solution;
   (b1) a high boiling point component separation step of separating high boiling point components at a distillation column as (b) a step of purifying the crude acrylic acid-containing solution;
   (c) a decomposition step of decomposing Michael adducts contained in the high boiling point components to generate acrylic acid; and
   (d) a collection step of collecting the acrylic acid generated in the decomposition step (c), wherein a column bottom of the distillation column at the high boiling point component separation step (b1) has a temperature of 90 to 130° C., a residence time of a column bottom solution is 2 to 30 hours, and a ratio of a mass of solution fed to the distillation column to a mass of extraction solution from the column bottom of the distillation column is 5 to 20, and
   a proportion of an amount of maleic acid to a sum of maleic acid and maleic anhydride in the high boiling point components fed from the high boiling point component separation step (b1) to the decomposition step (c) satisfies equation (1) below:

$$\frac{[\text{Maleic acid (mass)}]}{[\text{Maleic acid (mass)}] + [\text{Maleic anhydride (mass)}]} \times 100 \leq 70\%. \quad (1)$$

2. A method for producing acrylic acid according to claim 1, further comprising (b2) a crystallization purification step of separating crystals obtained by crystallizing acrylic acid in the crude acrylic acid-containing solution from residual mother liquid as an additional step of purifying the acrylic acid-containing solution (b), wherein at least one portion of the residual mother liquid obtained in the crystallization purification step (b2) is fed to the high boiling point component separation step (b1).

3. A method for producing acrylic acid according to claim 2, wherein a column bottom solution obtained in the high boiling point component separation step (b1) is fed to the decomposition step (c), a portion of a distillate obtained in the decomposition step (c) is fed to the high boiling point component separation step (b1), and a distillate obtained in the high boiling point component separation step (b1) and/or the distillate obtained in the decomposition step (c) are fed to the absorption step (a).

4. A method for producing acrylic acid according to claim 1, wherein a concentration of the Michael adducts in the high boiling point components fed to the decomposition step (c) is 20 to 60% by mass.

5. A method for producing acrylic acid according to claim 1, wherein the decomposition step (c) is carried out by a reaction-distillation process.

6. A method for producing acrylic acid according to claim 5, wherein the decomposition step (c) according to the reaction-distillation process is carried out at a reflux ratio of 0.5 to 6 using a shelf plate distillation column.

7. A method for producing acrylic acid according to claim 6, wherein the shelf plate distillation column has 3 or more of theoretical stages, and the position of 70 to 100% of total theoretical stages setting a column top side of the shelf plate distillation column as a base point is heated at 125° C. or less.

8. A method for producing acrylic acid according to claim 6, wherein the shelf plate distillation column is equipped with a tray having opening with a hole diameter of 10 to 50 mm.

9. A method for producing acrylic acid according to claim 1, wherein the decomposition step (c) uses a forced circulation type heat exchanger, heats the high boiling point components fed to the decomposition step (c) to 155 to 220° C., and controls temperature difference between a heat source of the forced circulation type heat exchanger and the high boiling point components heated by the forced circulation type heat exchanger at 15 to 80° C.

10. A method for producing acrylic acid according to claim 1, whereby the decomposition step (c) is carried out in a presence of an N-oxyl compound.

11. A method for producing acrylic acid according to claim 1, wherein all of a distillate obtained in the decomposition step (c) is fed to the high boiling point component separation step (b1) and fed to the absorption step (a) through the high boiling point component separation step (b1).

12. A method for producing acrylic acid according to claim 11, wherein a concentration of maleic acid in the distillate fed to the absorption step (a) is 2% by mass or less.

* * * * *